(12) United States Patent
Burba et al.

(10) Patent No.: US 7,285,096 B2
(45) Date of Patent: Oct. 23, 2007

(54) ULTRASOUND PROBE POSITIONING IMMERSION SHELL

(75) Inventors: Thomas A. Burba, Plymouth, MN (US); David R. Hardten, Orono, MN (US); Thomas C. Prager, Wimberley, TX (US)

(73) Assignee: ESI, Inc., Plymouth, MN (US)

( * ) Notice: Subject to any disclaimer, the term of this patent is extended or adjusted under 35 U.S.C. 154(b) by 887 days.

(21) Appl. No.: 10/706,554

(22) Filed: Nov. 12, 2003

(65) Prior Publication Data

US 2005/0101869 A1    May 12, 2005

(51) Int. Cl.
    *A61B 8/14* (2006.01)
(52) U.S. Cl. .................. 600/459; 600/452
(58) Field of Classification Search .......... 600/318, 600/356, 399–406, 437–438, 452–454, 459, 600/489, 500, 558
See application file for complete search history.

(56) References Cited

U.S. PATENT DOCUMENTS

| | | | | |
|---|---|---|---|---|
| 3,771,660 A | * | 11/1973 | Smith | ............ 210/232 |
| 3,945,381 A | * | 3/1976 | Silver | ............ 604/301 |
| 4,484,569 A | * | 11/1984 | Driller et al. | ............ 600/439 |
| 4,907,595 A | * | 3/1990 | Strauss | ............ 600/452 |
| 4,930,512 A | * | 6/1990 | Henriksen et al. | ............ 600/452 |
| 5,137,029 A | * | 8/1992 | Parra | ............ 600/558 |
| 6,315,727 B1 | * | 11/2001 | Coleman et al. | ............ 600/452 |

* cited by examiner

*Primary Examiner*—Francis J. Jaworski
(74) *Attorney, Agent, or Firm*—Hugh D. Jaeger, Esq.

(57) ABSTRACT

An ophthalmologic appliance being an ultrasound probe positioning immersion shell for use in ultrasonic measurement of axial length of the eye ophthalmology and other procedures. Support members in an upper chamber and a lower chamber each provides accommodating support along and about a central axis of the ultrasound probe positioning immersion shell and about vertically spaced regions of ultrasound probes to provide for perpendicular alignment of ultrasound probes to the corneal plane. Vents in the chamber structure allow for introduction of fluid medium and for the expelling of air from the chambers to inhibit bubble formation.

58 Claims, 16 Drawing Sheets

ULTRASOUND PROBE POSITIONING IMMERSION SHELL

CROSS REFERENCES TO RELATED APPLICATIONS

None.

BACKGROUND OF THE INVENTION

1. Field of the Invention

The present invention is an ultrasound probe positioning immersion shell that positions and aligns a diagnostic or therapeutic device, such as an ultrasound transducer probe, for the purpose of immersion of the eye for ultrasound axial length measurement, anterior chamber depth measurement, retinal detail measurement, or other diagnostic or therapeutic applications requiring alignment with the long axis of the eye.

2. Description of the Prior Art

There are several situations in the treatment of an ophthalmic patient that require a diagnostic ultrasound examination providing detailed information of the anatomical structures of the eye. This information enables the physician to provide the best possible care for a large variety of ocular disorders.

The most frequent use of ultrasound in ophthalmology is the axial eye length A-scan used to measure the eye prior to cataract surgery. A synonym for this type of A-scan is biometry. This measurement of an eye's axial length provides one of the three important values needed to calculate the appropriate power of an intraocular lens (IOL) implant after cataract removal. An inaccurate axial length measurement of just one millimeter can result in a post-operative optical error of three diopters, enough to necessitate a second surgery. Cataract removal and insertion of an intraocular lens (IOL) is performed over 1.5 million times a year in the U.S.

Two of the most commonly used techniques to perform axial eye length measurements are as follows:

a. Applanation, a contact technique; and, b. Immersion, an ultrasound, non-contact technique.

With the contact method, the axial length is measured with the ultrasound probe applanated on the center of the cornea. The biometrist must ensure that neither ointment nor excess fluid (e.g., anesthetic drops or tears) are present on the cornea prior to beginning the examination, since even a small amount of fluid may lead to erroneous axial length readings. The contact technique can be performed by applanation (chin rest method) or by hand (hand-held method). Disadvantages of the contact technique include both corneal compression and the possibility of corneal abrasion. The anterior chamber depth must be evaluated in each echogram since shallowing of the chamber occurs when the cornea is indented. Further, due to examiner parallax or alignment problems, it is often difficult to be sure measurements are taken from the center of the cornea.

The immersion non-contact biometry method is the preferred method of accurately measuring the length of the eye using a special shell that provides a liquid bath between the front surface of the eye (cornea) and the measuring ultrasound probe. The unique feature about the immersion method is that the ultrasound probe never actually touches the eye. This has value since one of the most common errors made while performing an applanation (contact) axial eye length A-scan is the compression or flattening of the cornea, producing a falsely short measurement. This technique is also best for patients with blepharospasm and fixation difficulties.

The three fundamental advantages of the immersion method are the following:

a. the capability to prevent inaccuracies due to corneal compression by eliminating the need to touch the cornea;

b. the capability to reproduce the measurement more readily; and, c. the capability to use echoes from the cornea for aligning the sound beam along the visual axis, thereby providing additional assurance of a measurement to the macula.

With the advancement in IOL design and manufacturing, a more precise axial length measurement of the eye is required for determining the correct IOL power required for optimal pseudophakic correction. An inaccurate axial length measurement of only 1 mm can result in a significant post-operative refractive error. The ultrasound manufacturers have improved the A-scan equipment with upgraded hardware and software for measuring eye length with the transducer immersed in a liquid medium. The biometry instrument converts the time readings into millimeter axial length. When using the immersion technique, these A-scan improvements require that the ultrasound probe tip be placed at a fixed and specified distance from the corneal surface. For accurate measurements, it is essential that the ultrasound probe remains perpendicular to the visual axis while the transducer is submersed. It is equally important for the liquid medium between the corneal surface and the transducer to be free of trapped air bubbles. The presence of air bubbles can disrupt the sound wave transmission and interfere with axial length measurement.

To keep the eye submersed in a liquid medium during biometry, various cylindrical shells of different shapes are used in immersion A-scan. All have shortcomings.

Hansen Shell

The Hansen shell is simply a plastic cylinder open at both ends incorporated in a two-handed procedure requiring skill to master. The Hansen shell is inserted under the eyelids and hand-held while the liquid medium is poured from the top submerging the transducer and eye. Because the ultrasound probe is free to move, it can be easily moved vertically and tilted, resulting in erroneous measurements. Further, a viscous solution, Goniosol, is required, which is expensive and leaves a vision-blurring film. Achieving accurate measurements using this shell design is difficult to master.

Kohn Shell

The Kohn shell has an hourglass shape with the ultrasound probe inserted to the constriction. A port including a metal tube and hose is located at the bottom portion or lower chamber of the shell for introducing the liquid medium. The ultrasound probe and shell meet at one location with a larger diameter opening at the top of the shell. This can result in vertical and angled error due to a single fulcrum contact point, as with mating two cones with different dimensions and angles. Any dimensional difference between the ultrasound probe shape and the shell constriction increases the likelihood for the ultrasound probe to be tilted and/or positioned at a different height.

This Kohn shell design forms two chambers once the ultrasound probe is inserted, and a "cork effect" occurs at the contact point between the ultrasound probe and shell constriction. The liquid medium then must be injected after the shell is on the eye through the port located in the lower chamber between the constriction and the bottom of the shell contacting the eye. This reduces the ability to visually place the shell and ultrasound probe on the eye due to the port and any connected tubing blocking the view. Furthermore, due to the ultrasound probe blocking the air from escaping from the lower chamber, a large air bubble can be easily trapped in the lower chamber and prevent an ultrasound axial length measurement.

Prager Scleral Shell

Another current design is the Prager scleral shell. This is a polycarbonate plastic cylinder with a flanged end that contacts the eye. To accommodate the ultrasound probe, the upper portion of the shell is bored out in the center with an inner diameter slightly larger than the ultrasound probe to maintain orientation. A setscrew located at the top of the shell is then tightened against the probe to preclude the probe from protruding out the shell bottom and potentially contacting the cornea. The probe tip can be placed at any height from the cornea. This requires the operator to carefully inspect the ultrasound probe height position before every ultrasound exam. If the ultrasound probe tip is either too low or too high, a faulty reading will occur. Furthermore, the ultrasound probe can be easily canted from the perpendicular position in the shell when the setscrew is tightened. To fill the shell with the liquid medium, a metal port or filler tube is press fit into the shell wall. The metal port or filler tube is inserted into PVC tubing or a butterfly needle is inserted into the metal port or filler tube. Any sharp object in close proximity to the eye is considered a safety issue. Typically, multiple holes are drilled into the wall of the lower portion of the shell for air to escape as the liquid enters the lower portion of the shell.

SUMMARY OF THE INVENTION

The general purpose of the present invention is to provide an ultrasound probe positioning immersion shell. To achieve the objectives for correct ultrasound probe positioning during immersion A-scan, an ultrasound probe positioning immersion shell, a unique immersion shell, has been developed. The ultrasound probe positioning immersion shell consistently places the ultrasound probe perpendicular to and at the correct distance from the corneal plane. The ultrasound probe positioning immersion shell has a fluid flow arrangement to ensure suitable filling of a lower chamber while minimizing air bubble formation which can disrupt or otherwise influence the ultrasound measuring process. The preferred methods to achieve the perpendicular ultrasound probe position are to have one continuous guide or, preferably, to have two or more separate opposed guide rings which can be externally and internally located with each having centrally located structures providing at least three arcuate guide surfaces for intimate contact with the cylindrical or tapered shape of an ultrasound probe, respectively. The configuration of each of the externally and internally located guide rings includes centrally located arcuate guide surfaces which accommodate the ultrasound probe and, additionally, at least include three vents which can be arcuate, which are offset from the centerline of the ultrasound probe positioning immersion shell, and which intersect the centrally located arcuate guide surfaces, thereby creating a scallop-like pattern. This pattern creates at least three points of ultrasound probe contact at each guide ring location and at least three vents about the intersection of the ultrasound probe and the respective external and internal guide rings. Two or more guide rings, used for positioning the ultrasound probe, result in partial defining of separate internal upper and lower chambers, where the upper chamber is between the external guide ring, the internal guide ring and an upper cylindrical body, and where the lower chamber, which is open at one end, is bounded by the internal guide ring and a lower cylindrical body and a lip. The vents in the internal guide ring allow for the transfer of liquid medium to drain from the upper chamber to the lower chamber. The external guide ring pattern allows for air pressure equalization to ambient air when liquid medium is introduced and when the ultrasound probe is centered in the external guide ring. Self-positioning of the ultrasound probe transducer is accomplished by the arcuate guide surfaces of the external and internal guide rings contacting the ultrasound probe at a minimum of two separate body regions to ensure perpendicular positioning of the ultrasound probe in the ultrasound probe positioning immersion shell. A fluid transfer port located in the upper portion of the ultrasound probe positioning immersion shell allows for various methods of filling the liquid medium. The fluid transfer port is located away from the base of the ultrasound probe positioning immersion shell so that it will be away from the eye to improve operator visualization during placement of the instrument. The ultrasound probe positioning immersion shell can be fashioned of transparent material to monitor placement on the eye and to monitor the liquid medium level.

The ultrasound probe positioning immersion shell self-positions the ultrasound probe in the ultrasound probe positioning immersion shell perpendicular to the ultrasound probe positioning immersion shell lower chamber lip horizontal plane and places the ultrasound probe at a specified height from the corneal surface to optimize axial length ultrasound measurement. The geometry and size of the external arcuate guide surfaces and internal arcuate guide surfaces form an automatic stop with respect to depth and also provide a safety feature that does not allow the ultrasound probe to be placed lower than the specified depth for an optimum A-scan, thereby avoiding accidental contact with the eye. After the ultrasound probe is inserted into the ultrasound probe positioning immersion shell to the automatic stop position, the ultrasound probe positioning immersion shell is then placed on the eye. Liquid medium is filled through the fluid transfer port with low pressure to eliminate the possibility of eye tissue damage from the fluid flowing into the ultrasound probe positioning immersion shell. The external and internal arcuate vents greatly reduce the possibility of air bubble formation.

According to one or more embodiments of the present invention, there is -provided an ultrasound probe positioning immersion shell including external and internal support including arcuate guide surfaces on external and internal guide rings for alignment with an ultrasound probe, vents located within the external and internal guide rings, upper and lower chambers for transfer or containment of liquid or other medium, a lip for contact with the limbus or area adjacent to the cornea of an eye, and a port for introduction of liquid or other medium into the ultrasound probe positioning immersion shell, as well as other features.

One significant aspect and feature of the present invention is an ultrasound probe positioning immersion shell which is fully vented.

Another significant aspect and feature of the present invention is an ultrasound probe positioning immersion shell which eliminates or minimizes air bubble formation.

Still another significant aspect and feature of the present invention is an ultrasound probe positioning immersion shell which incorporates sets of guide surfaces at different levels or locations to align an ultrasound probe to its central axis.

Yet another significant aspect and feature of the present invention is an ultrasound probe positioning immersion shell which positions an ultrasound probe at a precise distance from the corneal plane of an eye.

A further significant aspect and feature of the present invention is an ultrasound probe positioning immersion shell which will not allow an ultrasound probe to positionally invade a cornea of an eye.

Still another significant aspect and feature of the present invention is geometry which limits the travel of an ultrasound probe along the central axis and acts as a stop.

A still further significant aspect and feature of the present invention is an ultrasound probe positioning immersion shell which allows for liquid medium introduction at a level distant from the eye.

Another significant aspect and feature of the present invention is a fluid transfer port which can accommodatingly be incorporated by itself or with the use of a Luer fitting, a fitted filler tube, an integral molded rigid filler tube, or an integral molded rigid filler tube and permanently attached flexible filler tube.

Another significant aspect and feature of the present invention is an ultrasound probe positioning immersion shell which can be transparent to monitor and observe liquid medium levels.

An alternate embodiment of the present invention involves a one-piece ultrasound probe positioning immersion shell, the significant aspects and features of which additionally include:
a. vertically aligned guides for contacting of and for support of an ultrasound probe where the guides include upper guide edges, lower guide edges and arcuate, angled or other geometrically configured guide edges therebetween;
b. a keeper tab for ensuring the alignment of an inserted ultrasound probe against vertically aligned guides; and,
c. a keeper tab for securing an inserted ultrasound probe within the one-piece ultrasound probe positioning immersion shell.

Having thus described embodiments of the present invention and pointed to significant aspects and features thereof, it is the principal object of the present invention to provide an ultrasound probe positioning immersion shell.

BRIEF DESCRIPTION OF THE DRAWINGS

Other objects of the present invention and many of the attendant advantages of the present invention will b readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
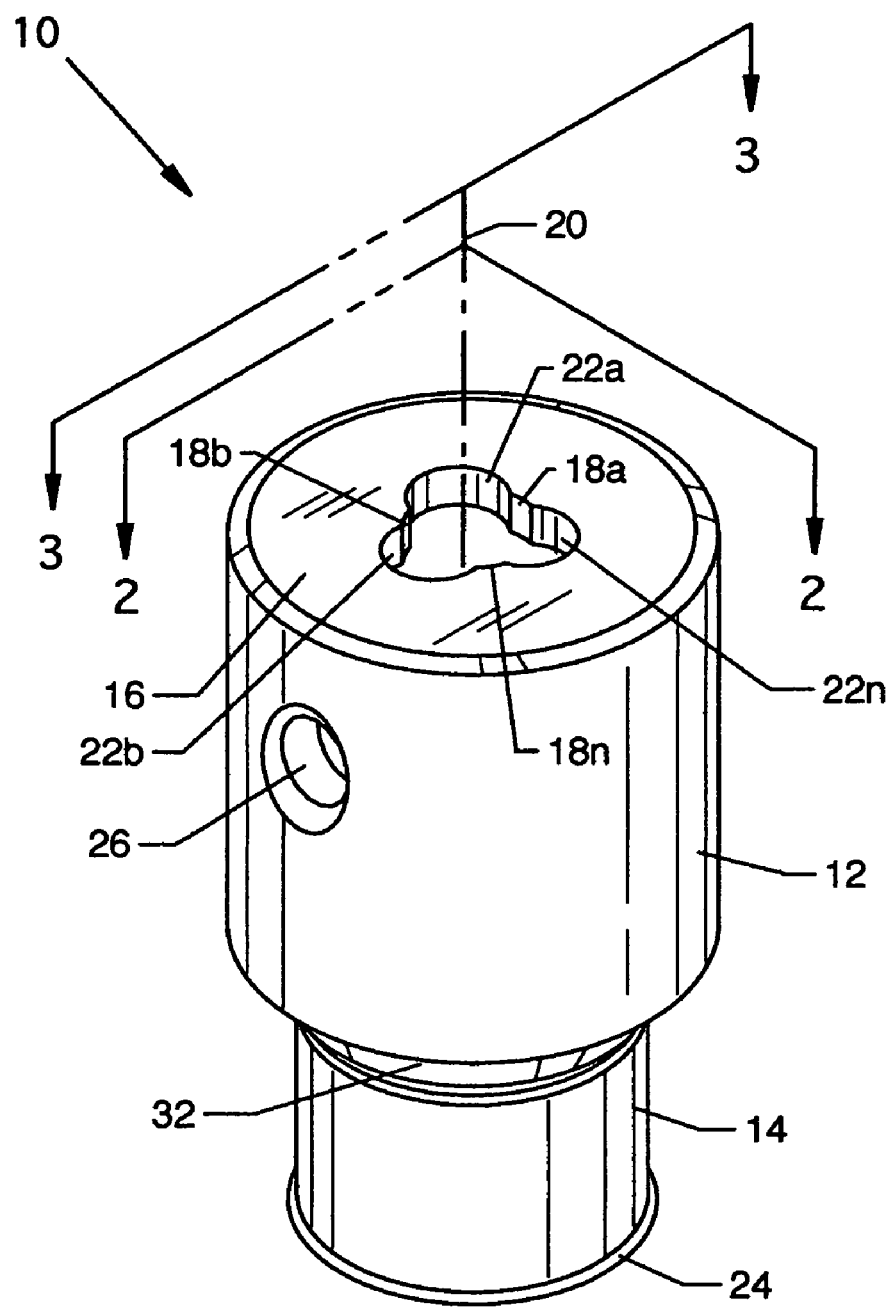
FIG. 1 is an isometric view of the ultrasound probe positioning immersion shell, the present invention.
Figure 2:
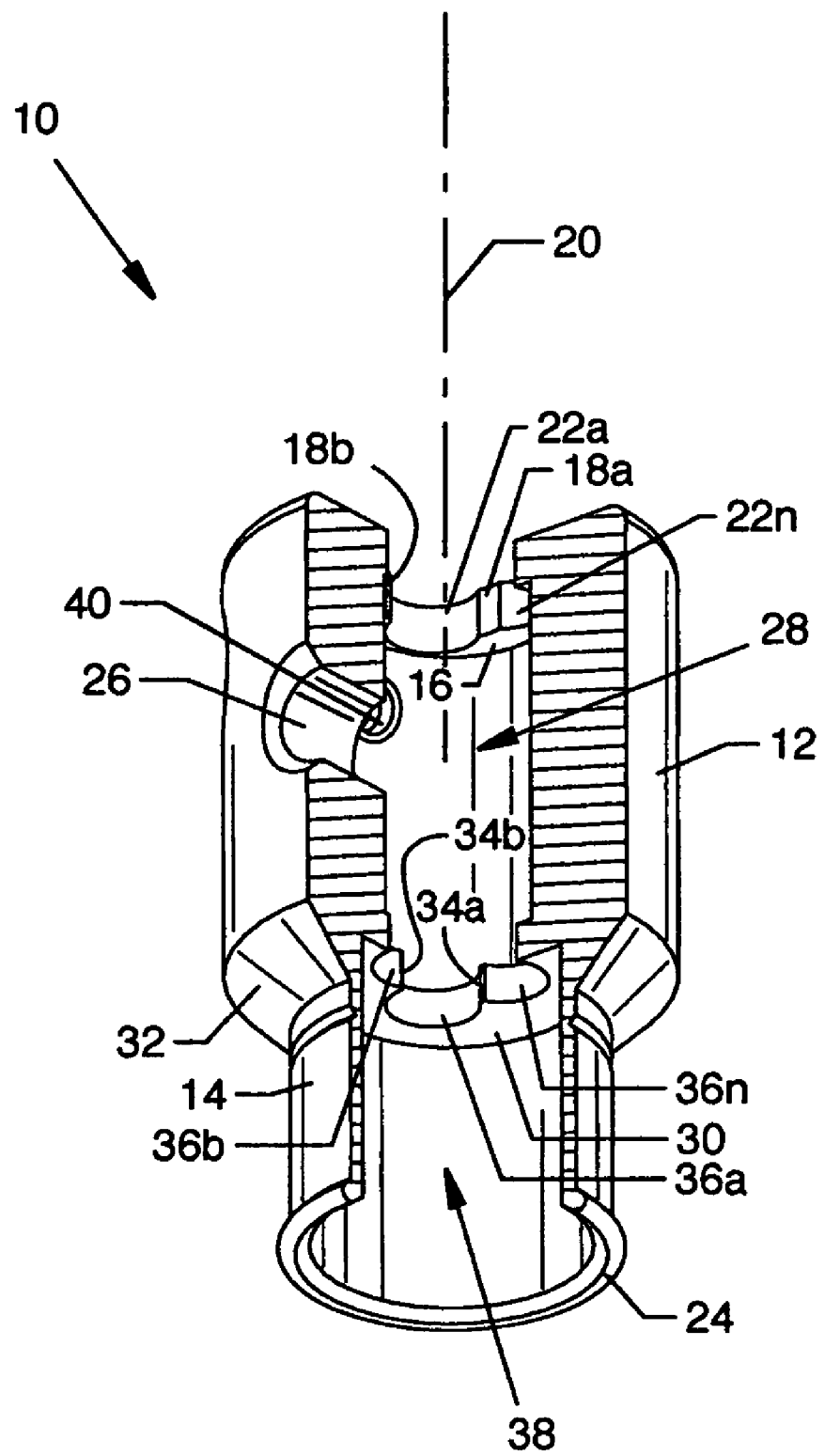
FIG. 2 is a re-oriented cutaway view in partial cross section along line 2-2 of FIG. 1.

FIG. 1 is an isometric view of the ultrasound probe positioning immersion shell 10, and FIG. 2 is a re-oriented cutaway view in partial cross section along line 2-2 of FIG. 1 showing additional internally located elements of the ultrasound probe positioning immersion shell 10. Outwardly and readily visible elements of the ultrasound probe positioning immersion shell 10 include an upper cylindrical body 12 tapering to a lower cylindrical body 14, an external guide ring 16 extending across the upper region of the upper cylindrical body 12, a plurality of guide surfaces 18a-18n, preferably being arcuate, extending through the external guide ring 16 and having a common radius centered along the central axis 20 of the ultrasound probe positioning immersion shell 10, a plurality of external vents 22a-22n, preferably being arcuate, extending through the external guide ring 16 and having like radii offset from the central axis 20 of the ultrasound probe positioning immersion shell 10 and intersecting the plurality of guide surfaces 18a-18n, a lip 24 at the lower region of the lower cylindrical body 14, and a fluid transfer port 26 extending through the upper cylindrical body 12 to communicate with an upper chamber 28 (FIG. 2) of the ultrasound probe positioning immersion shell 10. The fluid transfer port 26 can be incorporated into use by itself or with the use of a Luer fitting, a fitted filler tube, an integral molded rigid filler tube, or an integral molded rigid filler tube and permanently attached flexible filler tube.

Although the guide surfaces 18a-18n are preferably arcuate, other geometrically-shaped guide surfaces, such as planar surfaces, vertical edges or other suitably located geometrically configured elements and the like being appropriately spaced from the central axis 20, can be utilized without departing from the teachings and scope of the instant invention. Also, the external vents 22a-22n preferably are arcuate; however, other geometrically-shaped external vents incorporating planar or other geometrically configured surfaces to form external vents and the like about the plurality of guide surfaces 18a-18n and being appropriately located outwardly from and non-interfering with the function of the plurality of guide surfaces 18a-18n can be utilized without departing from the teachings and scope of the instant invention.

Various materials can be used in manufacturing the ultrasound probe positioning immersion shell 10, including, but not limited to, acrylic, polycarbonate Ultem, or other plastics which can be transparent, and stainless steel, aluminum, or other metals. The ultrasound probe positioning immersion shell 10 can be manufactured by machining or injection molding.

FIG. 2 reveals additional elements of the ultrasound probe positioning immersion shell 10, including an internal guide ring 30 located substantially adjacent to and interior to a tapered region 32 between the upper cylindrical body 12 and the lower cylindrical body 14 and extending across the lower region of the upper cylindrical body 12, as well as being co-located at the upper region of the lower cylindrical body 14. The structure of the internal guide ring 30 relates directly to that of the external guide ring 16 and opposingly aligns in a spaced relationship thereto and differs slightly in size as described herein. A plurality of guide surfaces 34a-34n, preferably being arcuate, extend through the internal guide ring 30 and have a common radius centered along the central axis 20 of the ultrasound probe positioning immersion shell 10, where such radius is appropriately less than the radius incorporated in relation to the plurality of guide surfaces 18a-18n of the external guide ring 16. A plurality of internal vents 36a-36n, preferably being arcuate, extending through the internal guide ring 30 and having like radii offset from the central axis 20 of the ultrasound probe positioning immersion shell 10 and intersecting the plurality of guide surfaces 34a-34n are also included.

Although the guide surfaces 34a-34n are preferably arcuate, other geometrically-shaped guide surfaces, such as planar surfaces, vertical edges or other suitably located geometrically configured elements and the like being appropriately spaced from the central axis 20, can be utilized without departing from the teachings and scope of the instant invention. Also, the internal vents 36a-36n preferably are arcuate; however, other geometrically-shaped internal vents incorporating planar or other geometrically configured surfaces to form internal vents and the like about the plurality of guide surfaces 34a-34n being appropriately located outwardly from and noninterfering with function of the plurality of guide surfaces 34a-34n can be utilized without departing from the teachings and scope of the instant invention.

The external guide ring 16 and the internal guide ring 30, the elements of which are used for positioning an ultrasound probe, partially define the separate upper chamber 28 and a lower chamber 38, where the upper chamber 28 is bounded by the external guide ring 16, the internal guide ring 30 and the upper cylindrical body 12, and where the lower chamber 38, which is open at one end, is bounded by the internal guide ring 30, the lower cylindrical body 14, and the lip 24 at the outer extremity of the lower cylindrical body 14.

Alternatively, the internal guide ring 30 and associated elements can be located along the central axis 20 in a position proximal to the shown position, thereby varying the size, proportion and volume of the upper chamber 28 and the lower chamber 38. As such, being still located on the upper cylindrical body 12, the fluid transfer port 26 could be positioned more distally toward the tapered region 32 to a position distal to the internal guide ring 30; i.e., the internal guide ring 30 and the fluid transfer port 26 can assume different relative positions, whereby, with the elongation of the lower chamber 38, fluid can be introduced directly into the lower chamber 38 at a point below internal guide ring 30, but above the tapered region 32 where fluid ingress is distanced at least by the lower cylindrical body 14.

Figure 4:
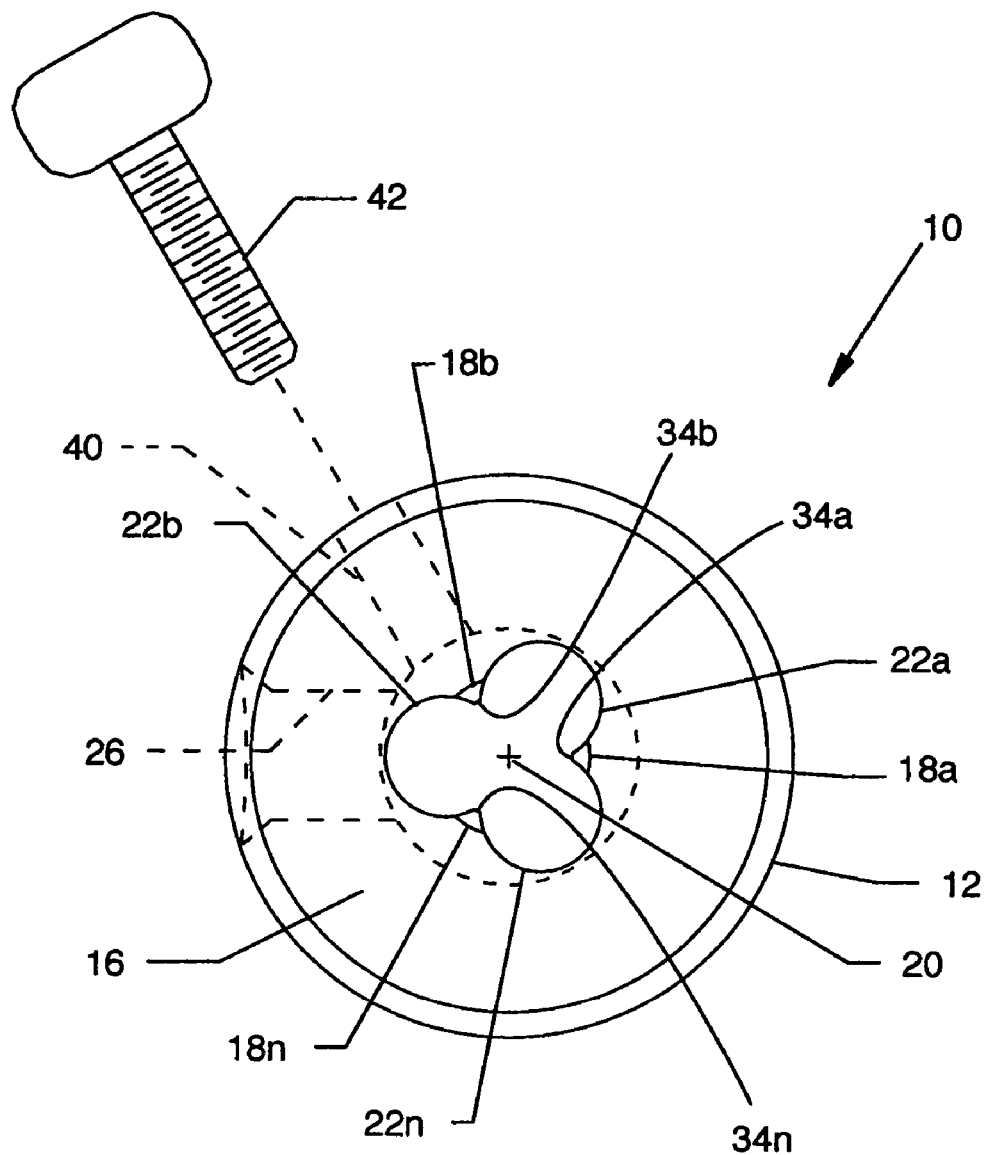
FIG. 4 is a top view of the ultrasound probe positioning immersion shell.

A threaded hole 40 extends through the upper cylindrical body 12 to accommodate a threaded fastening device 42, as shown in FIG. 4.

Figure 3:
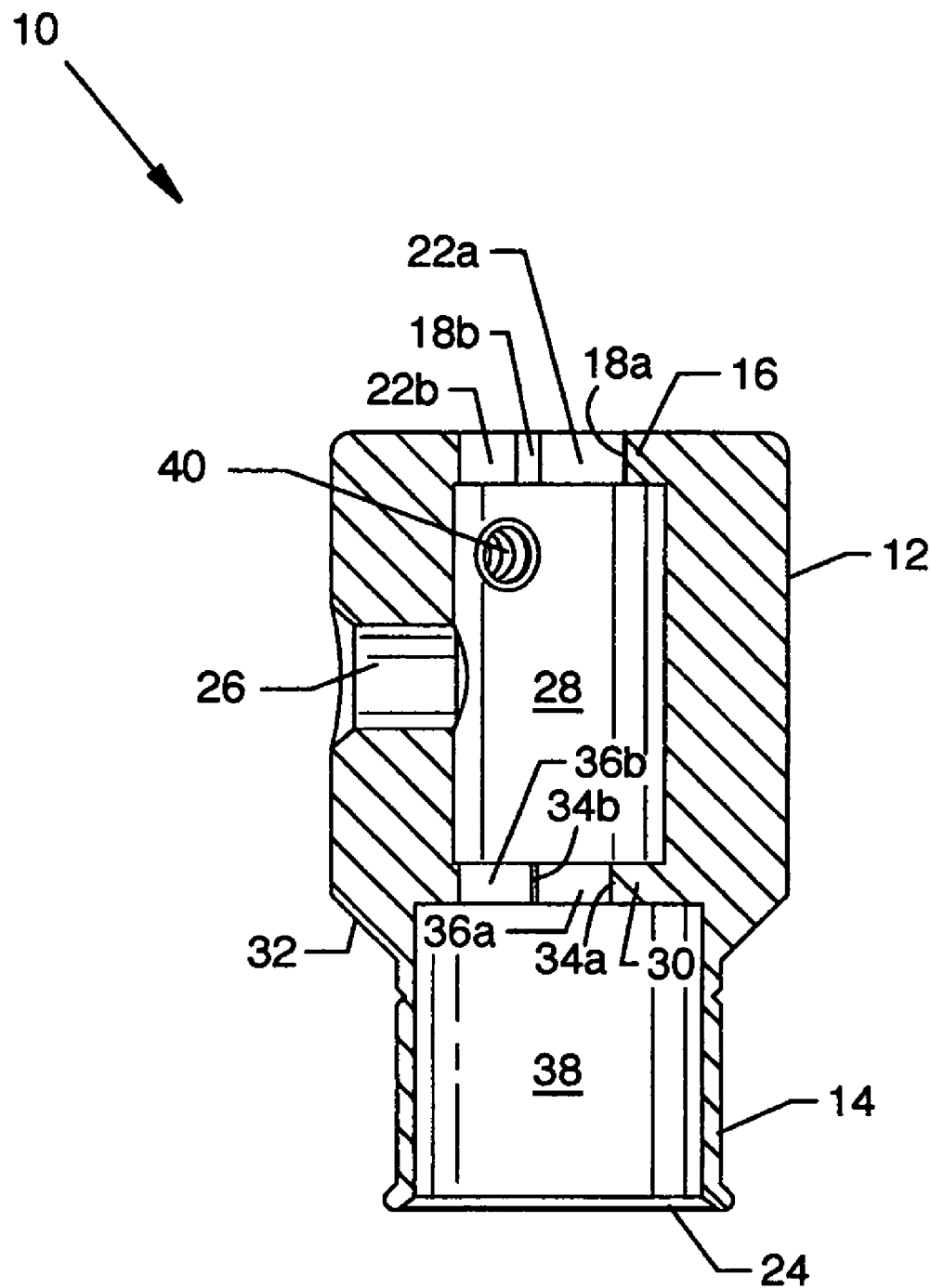
FIG. 3 is a cross section view of the ultrasound probe positioning immersion shell along line 3-3 of FIG. 1.

FIG. 3 is a cross section view of the ultrasound probe positioning immersion shell 10 along line 3-3 of FIG. 1.

FIG. 4 is a top view of the ultrasound probe positioning immersion shell 10. Shown in particular is the relationship of the guide surfaces 18a-18n offset from the central axis 20 to the guide surfaces 34a-34n offset from the central axis 20 where the guide surfaces 34a-34n have a lesser offset from the central axis 20 than the guide surfaces 18a-18n. Such a relationship provides for guidance of an ultrasound probe 44 (FIG. 6) along the central axis 20 of the ultrasound probe positioning immersion shell 10 where the guide surfaces 18a-18n and 34a-34n align the ultrasound probe 44 to the central axis 20 of the ultrasound probe positioning immersion shell 10 and where such a relationship forms a geometric configuration, which, due to diminishing offsets and corresponding geometry, forms a stop to limit travel of an ultrasound probe, such as the ultrasound probe 44, within the ultrasound probe positioning immersion shell 10. An optional fastening device 42, such as, but not limited to, a thumbscrew, set screw or other suitable device or the like, can be utilized in the threaded hole 40 to bear against the ultrasound probe 44, thus providing fixation of the ultrasound probe 44 within the ultrasound probe positioning immersion shell 10.

Figure 5:
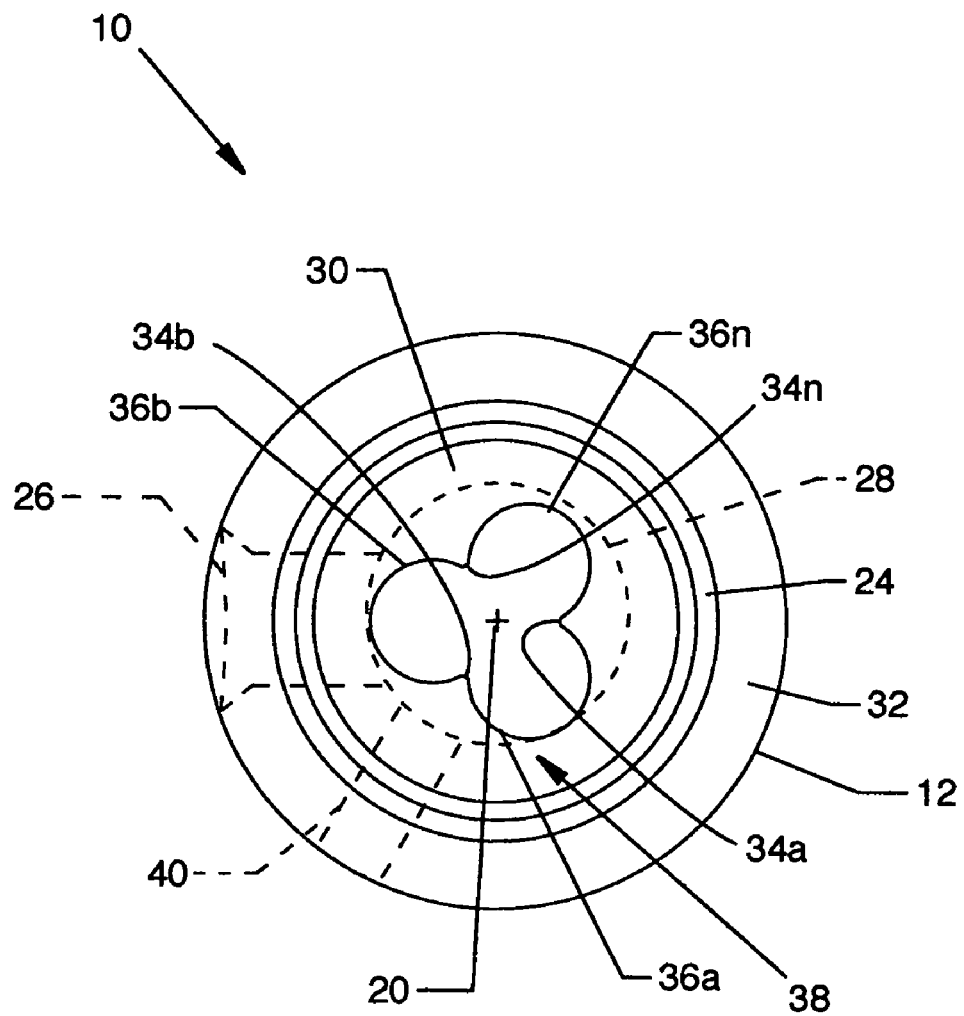
FIG. 5 is a bottom view of the ultrasound probe positioning immersion shell.

FIG. 5 is a bottom view of the ultrasound probe positioning immersion shell 10 showing the lower chamber 38 and the internal guide ring 30 in which the guide surfaces 34a-34n and the internal vents 36a-36n are located.

Figure 6:
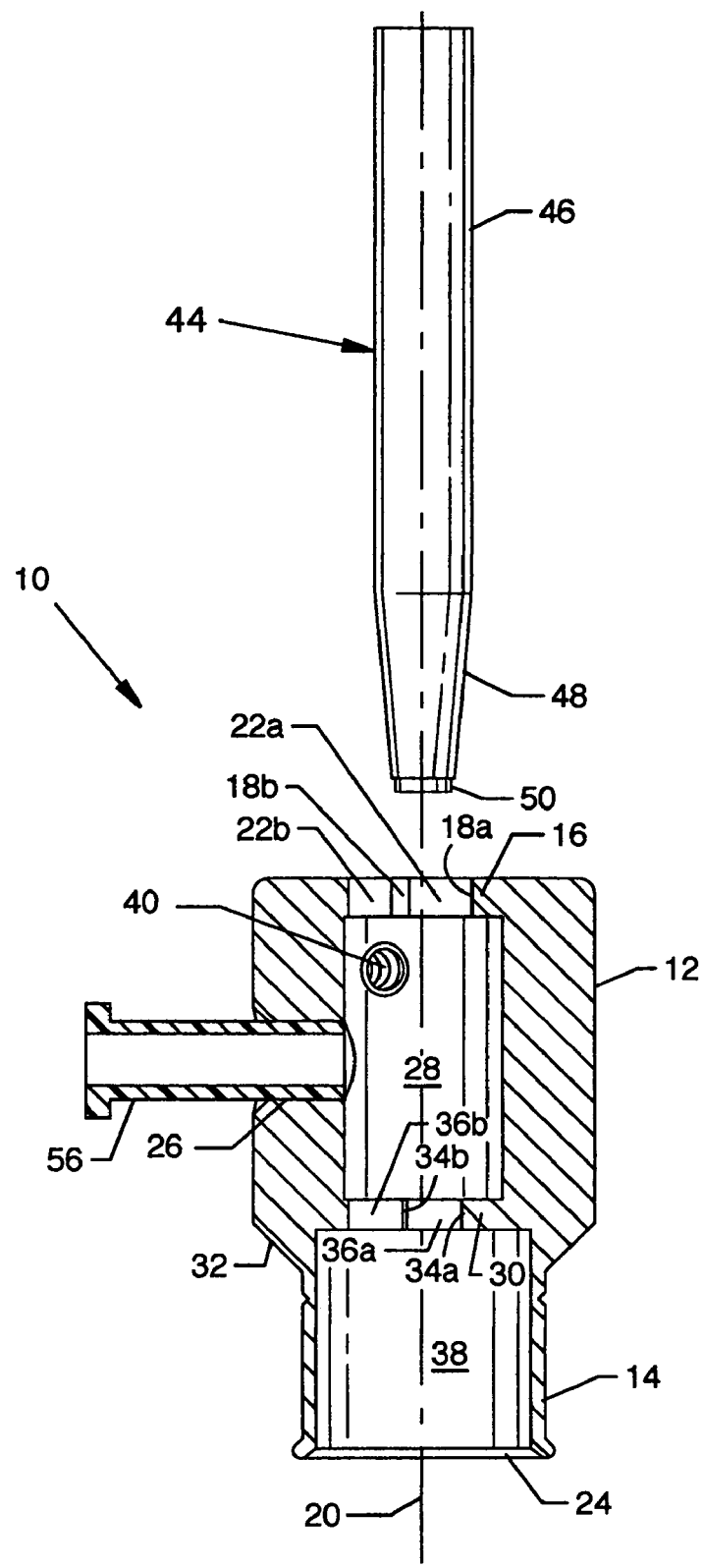
FIG. 6 illustrates an ultrasound probe in external alignment to the ultrasound probe positioning immersion shell which is shown in cross section along with a Luer fitting also shown in cross section.

FIG. 6 illustrates an ultrasound probe 44 in external alignment to the ultrasound probe positioning immersion shell 10. Elements of the ultrasound probe positioning immersion shell 10 are designed to support the ultrasound probe 44, which can be incorporated into use with the ultrasound probe positioning immersion shell 10. The ultrasound probe 44 includes a constant radius body region 46, a tapered body region 48, and a transducer 50 at one end of the tapered body region 48. Shown in particular is the relationship of the guide surface 18a located in the external guide ring 16 to the guide surface 34a located in the internal guide ring 30. Guide surface 18a is offset from the vertical axis 20 at a distance greater than the offset of the guide surface 34a from the vertical axis 20. Correspondingly and symmetrically, as shown in previous figures, guide surfaces 18b-18n are offset the same distance in correspondence to the offset of guide surface 18a from the vertical axis 20. Correspondingly and symmetrically, as shown in previous figures, guide surfaces 34b-34n are offset the same distance in correspondence to the offset of guide surface 34a from the vertical axis 20. Collectively, guide surfaces 18a-18n form a structure at the external guide ring 16 for supporting the constant radius body region 46 of ultrasound probe 44, and collectively, guide surfaces 34a-34n form a structure at the internal guide ring 30 for supporting the tapered body region 48 of ultrasound probe 44.

MODE OF OPERATION

Figure 7:
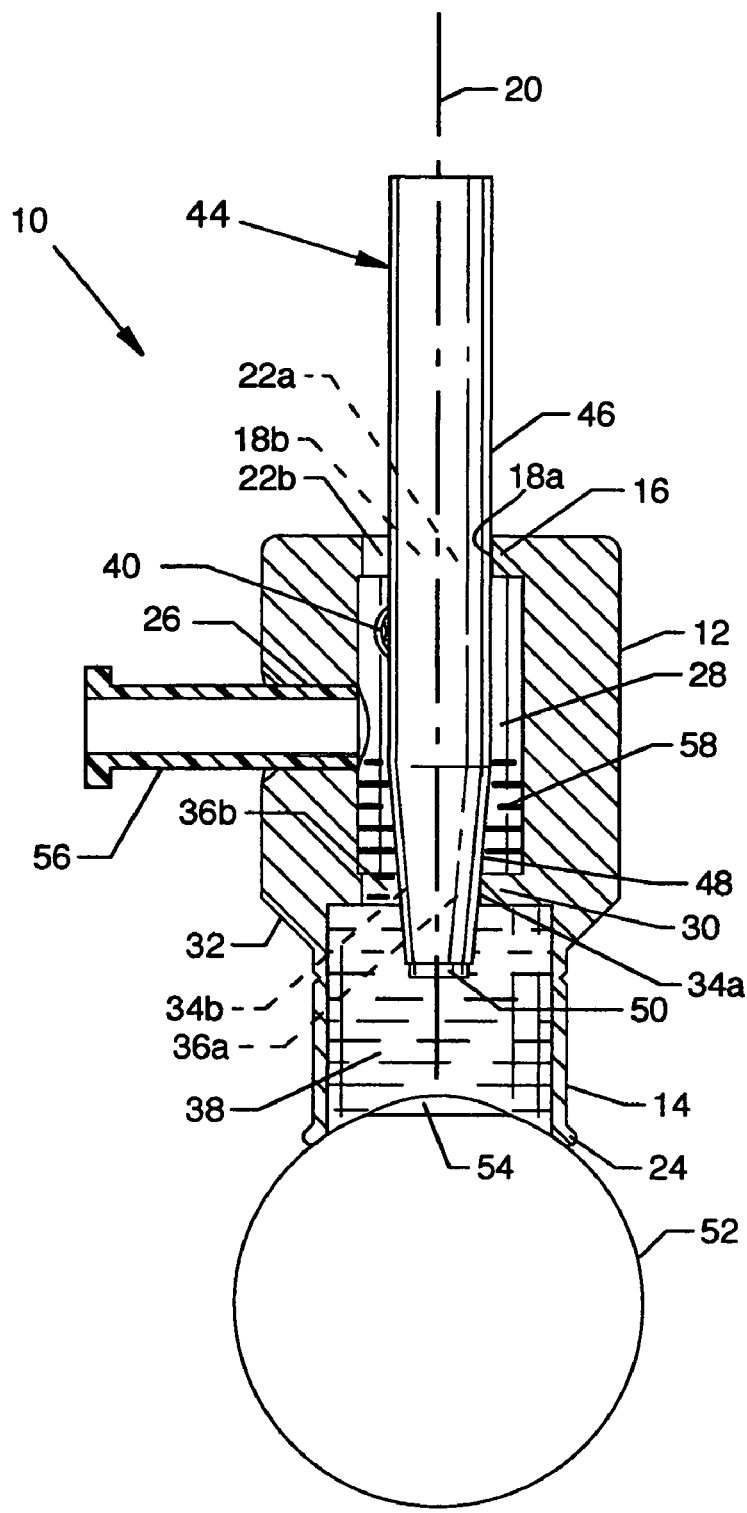
FIG. 7 is a view similar to FIG. 6 but illustrating the ultrasound probe aligned within the ultrasound probe positioning immersion shell for alignment with and for ultrasound measurements of an eye (shown schematically)

FIG. 7 best illustrates the mode of operation where an ultrasound probe 44 aligns within the ultrasound probe positioning immersion shell 10 for vertical alignment with and for ultrasound measurements of an eye 52 which is in contact with the lip 24 of the ultrasound probe positioning immersion shell 10. As previously described, the constant radius body region 46 of the ultrasound probe 44 aligns to the guide surfaces 18a-18n and along the central axis 20 of the ultrasound probe positioning immersion shell 10, and the tapered body region 48 of the ultrasound probe 44 stoppingly aligns along the central axis 20 of the ultrasound probe positioning immersion shell 10 to the guide surfaces 34a-34n, a distance along the central axis 20 which is predetermined by the relationship of the guide surfaces 34a-34n to the tapered body region 48 of the ultrasound probe 44, to position the transducer 50 of the ultrasound probe 44 the correct and suitable distance from the cornea 54 of the eye 52. Full support of the ultrasound probe 44 is provided at several levels, thus promoting stability of the ultrasound probe 44 with respect to the ultrasound probe positioning immersion shell 10. In particular, support of the constant radius body region 46 of the ultrasound probe 44 is provided by intimate but sliding contact with the guide surfaces 18a-18n, and support of the tapered body region 48 of the ultrasound probe 44 is provided by intimate contact with the guide surfaces 34a-34n. A Luer fitting 56, which can be male or female, is suitably connected to the fluid transfer port 26 for introduction of saline solution 58 or other suitable solution.

The invention user can directly observe correct placement of the ultrasound probe positioning immersion shell 10 on the eye 52 since the fluid transfer port 26 of the ultrasound probe positioning immersion shell 10 to which liquid filling apparatus is connected is located appropriately on the upper cylindrical body 12 away from the lower cylindrical body 14 and away from the surface of the eye 52. Correct placement of the ultrasound probe positioning immersion shell 10 can be further enhanced by the use of a clear plastic to form it. The use of clear plastic also enhances level monitoring of the liquid medium. The fluid transfer port 26 of the ultrasound probe positioning immersion shell 10 allows for the operator to use different means of supplying the liquid medium. Liquid medium, such as a saline solution 58, can be filled through the fluid transfer port 26 by a syringe directly through the fluid transfer port 26, by a syringe through a fitted filler tube connected to the transfer port 26, by an integral molded rigid filler tube, by a vial directly attached to the fluid transfer port 26, or by the illustrated Luer fitting 56 and a flexible filler tube attached to the fluid transfer port 26, which is connected to a container of liquid medium (not shown), or by other suitable delivery methods known in the art.

Introduction and flow of saline solution 58 (liquid medium) into and within the ultrasound probe positioning immersion shell 10 is unrestricted, first into the upper chamber 28, followed by passage or draining of saline solution 58 through the internal vents 36a-36n at the internal guide ring 30 into the lower chamber 38 for suitable immersion of the lower portions of the ultrasound probe 44, including at least the transducer 50 and preferably other portions of the ultrasound probe 44. As saline solution 58 enters the upper chamber 28 and subsequently the lower chamber 38, air residing in the upper chamber 28 and the lower chamber 38 is displaced by the incoming saline solution 58 and vented and expelled without restriction from the lower chamber 38, through the internal vents 36a-36n, through the upper chamber 28, and through the external vents 22a-22n in the external guide ring 16 at the top of the upper chamber 28. Fully vented upper and lower chambers 28 and 38 prevent back pressure buildup so that outflow of displaced air and exclusion of bubbles is not impeded.

The internal vents 36a-36n disperse the liquid flow pattern and create multiple paths for both the saline solution 58 to drain in one direction and for air to escape in another direction to and from the lower chamber 38, minimizing air bubble formation in the lower chamber 38 to provide bubble-free saline solution 58 between the transducer 50 of the ultrasound probe 44 and the cornea 54 and surrounding surface of the eye 52.

Figure 8:
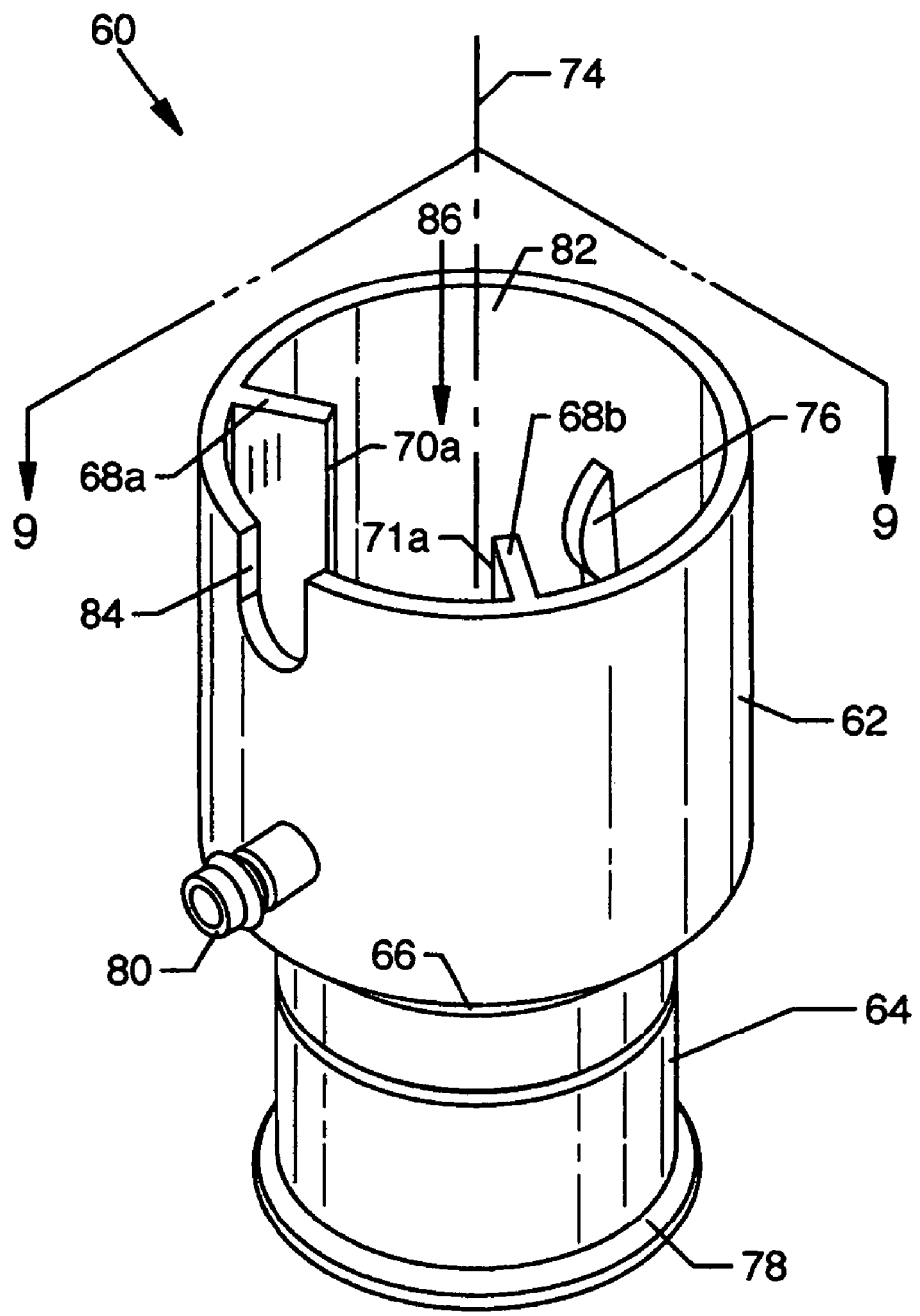
FIG. 8 is an isometric view of an alternative embodiment ultrasound probe positioning immersion shell.
Figure 9:
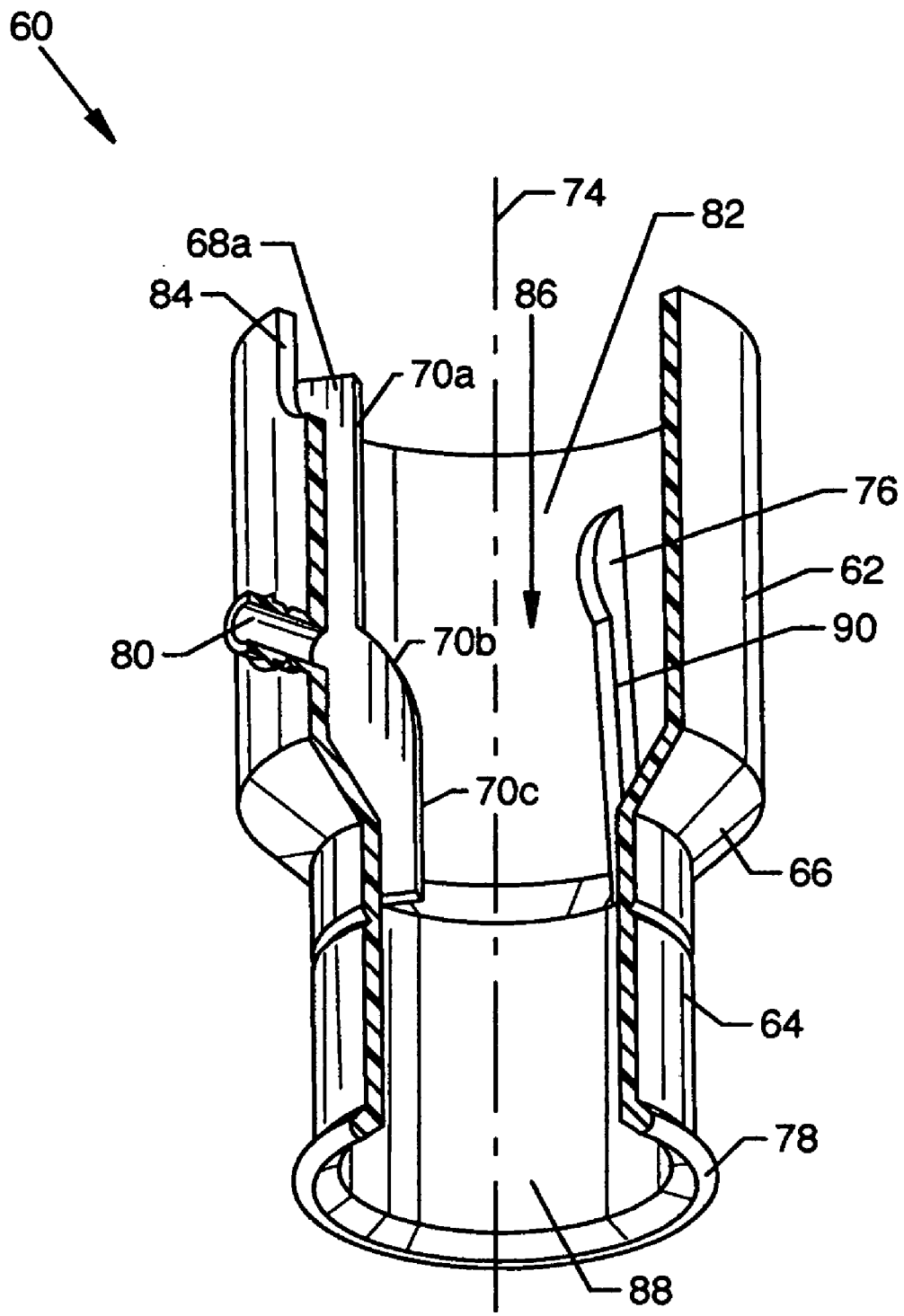
FIG. 9 is a re-oriented cutaway view in partial cross section along line 9-9 of FIG. 8 showing additional internally located elements of the alternative embodiment.

FIG. 8 is an isometric view of a one-piece ultrasound probe positioning immersion shell 60, an alternative embodiment, and FIG. 9 is a re-oriented cutaway view in partial cross section along line 9-9 of FIG. 8 showing additional internally located elements of the alternative embodiment. The one-piece ultrasound probe positioning immersion shell 60 preferably is molded of a suitable plastic material, preferably a clear plastic material, thus being able to utilize high output production techniques at a lower per unit cost than that of labor intensive machined ultrasound probe positioning immersion shells. Outwardly and readily visible elements of the ultrasound probe positioning immersion shell 60 include an upper cylindrical body 62 tapering to a lower cylindrical body 64 via a tapered intermediate body 66, a plurality of guides 68a-68b the greater portions of which extend inwardly from the upper cylindrical body 62 and smaller portions of which extend from portions of the tapered intermediate body 66 and the lower cylindrical body 64, and inwardly facing upper guide edges 70a and 71a located on the inner edges of the guides 68a-68b and offset from the central axis 74 for aligned contact with portions of an ultrasound probe 72, shown later in detail, being substantially in parallel alignment to the central axis 74 of the ultrasound probe positioning immersion shell 60 and in common to the locus of a radius centered along the central axis 74 of the ultrasound probe positioning immersion shell 60. Also shown is one end of a keeper tab 76 aligned substantially perpendicular and flexibly to the central axis 74 of the ultrasound probe positioning immersion shell 60, a lip 78 at the lower region of the lower cylindrical body 64, a fluid transfer port 80 extending through the upper cylindrical body 62 to communicate with an upper chamber 82 of the ultrasound probe positioning immersion shell 60, and a slot 84, the upper portion of which is open, extending through the upper region of the upper cylinder body 62. Grouped individual external and internal vents, such as previously described, are not included in this alternative embodiment; rather, the same venting function is provided by the interior of the upper cylindrical body 62, the tapered intermediate body 66, and the lower cylindrical body 64 and the lip 78, which offer and form a large vent 86 extending along and about the central axis 74 being bounded by the upper cylindrical body 62 and the tapered intermediate body 66 which form the upper chamber 82, and by the lower cylindrical body 64 and lip 78 which form a lower chamber 88 and, of course, by the interceding guides 68a-68b and the keeper tab 76 and a keeper tab arm 90 (FIG. 9).

Various materials can be used in manufacturing the ultrasound probe positioning immersion shell 60, including, but not limited to, plastics which can be clear, plastics including acrylic, polycarbonate Ultem, or other plastics, and stainless steel, aluminum, or other metals. The ultrasound probe positioning immersion shell 60 can be manufactured by machining or preferably by injection molding.

FIG. 9 in cross section reveals additional elements of the ultrasound probe positioning immersion shell 60 including the lower chamber 88 and the keeper tab arm 90, as well as other structure. FIG. 9 shows the upper cylindrical body 62, the tapered intermediate body 66, the lower cylindrical body 64, and the lip 78 which form the upper and lower chambers 82 and 88, respectively, which are open at opposing ends and which are in mutual communication where the upper chamber 82 is formed by and encompassed by the upper cylindrical body 62 and the tapered intermediate body 66 in combination, and where the lower chamber 88 is formed by and encompassed by the lower cylindrical body 64 and the lip 78 in combination.

The guides 68a-68b, the keeper tab 76, and the keeper tab arm 90 extend inwardly into the upper chamber 82 and portions of the lower chamber 88 from the surrounding structure, as previously described, thereby also extending into the vent 86. The guide 68a, in addition to the upper guide edge 70a, also includes a lower guide edge 70c offset less than the offset of the upper guide edge 70a from the central axis 74 and being substantially in parallel alignment to the central axis 74 of the ultrasound probe positioning immersion shell 60 and in common to the locus of the lesser radius being offset less than the offset of the upper guide edge 70a from the central axis 74. An arcuate guide edge 70b is located between the upper guide edge 70a and the lower guide edge 70c. The guide 68b is fashioned similarly and includes an upper guide edge 71a, a lower guide edge 71c, and an interceding arcuate guide edge 71b. The guides 68a and 68b, including the guide edges described above, provide guidance and support for the ultrasound probe 72, as later described in detail.

Although the upper, arcuate, and lower guide edges 70a-70c and 71a-71c, respectively, are shown in their respective geometrical shapes, other geometrically-shaped guide edges, such as arcuate surfaces, vertical edges, or other suitably located geometrically configured elements separately or in combination and the like being appropriately and similarly spaced from the central axis 74, can be utilized to accommodate the particular geometrical configuration of an ultrasound probe; i.e., the arcuate guide edges 70b and 71b could be angled surfaces or notched surfaces or other geometric configurations to suitably mate with and stoppingly accommodate the ultrasound probe geometrical configuration, without departing from the teachings and scope of the instant invention.

Figure 10:
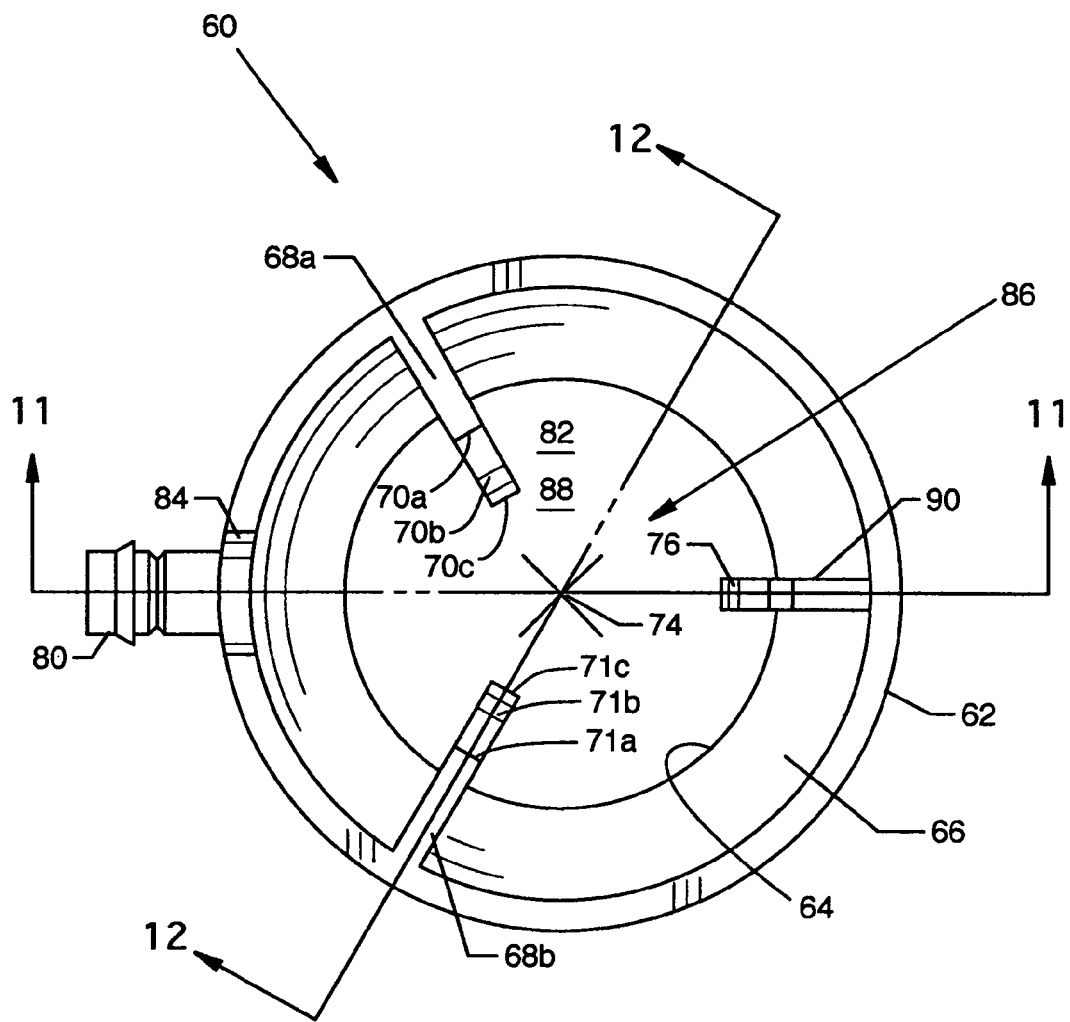
FIG. 10 is a top view of the alternative embodiment ultrasound probe positioning immersion shell.

FIG. 10 is a top view of the ultrasound probe positioning immersion shell 60 illustrating the offset of the upper guard edge 70a and the upper guard edge 71a from the central axis 74 and of the lesser offset of the lower guard edge 70c and the lower guard edge 71c from the central axis 74. Also shown is the vent 86 extending along and about the central axis 74. Also shown is the keeper tab 76 in angular opposition to the guides 68a and 68n.

Figure 11:
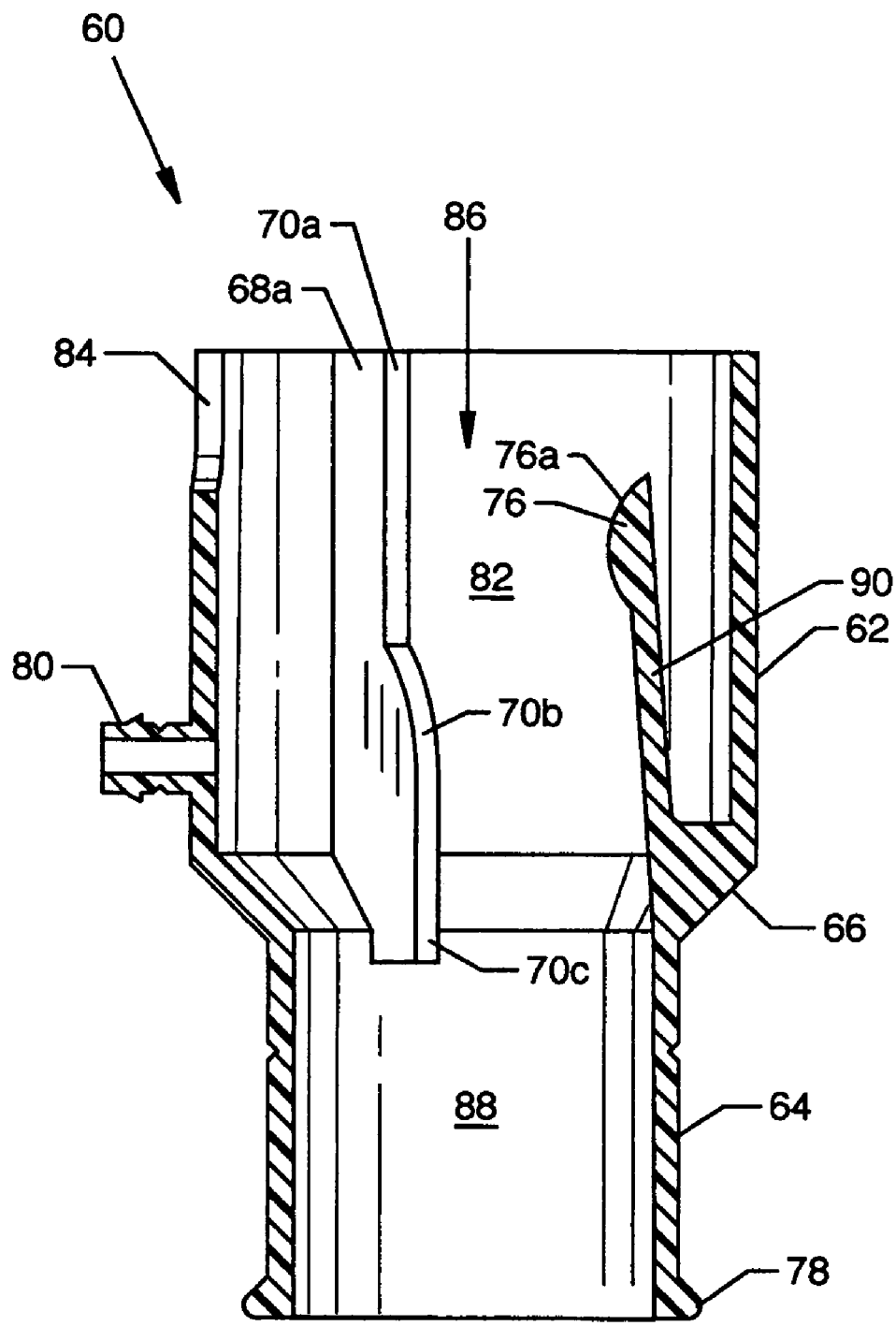
FIG. 11 is a cross section view of the alternative embodiment ultrasound probe positioning immersion shell along line 11-11 of FIG. 10.
Figure 15:
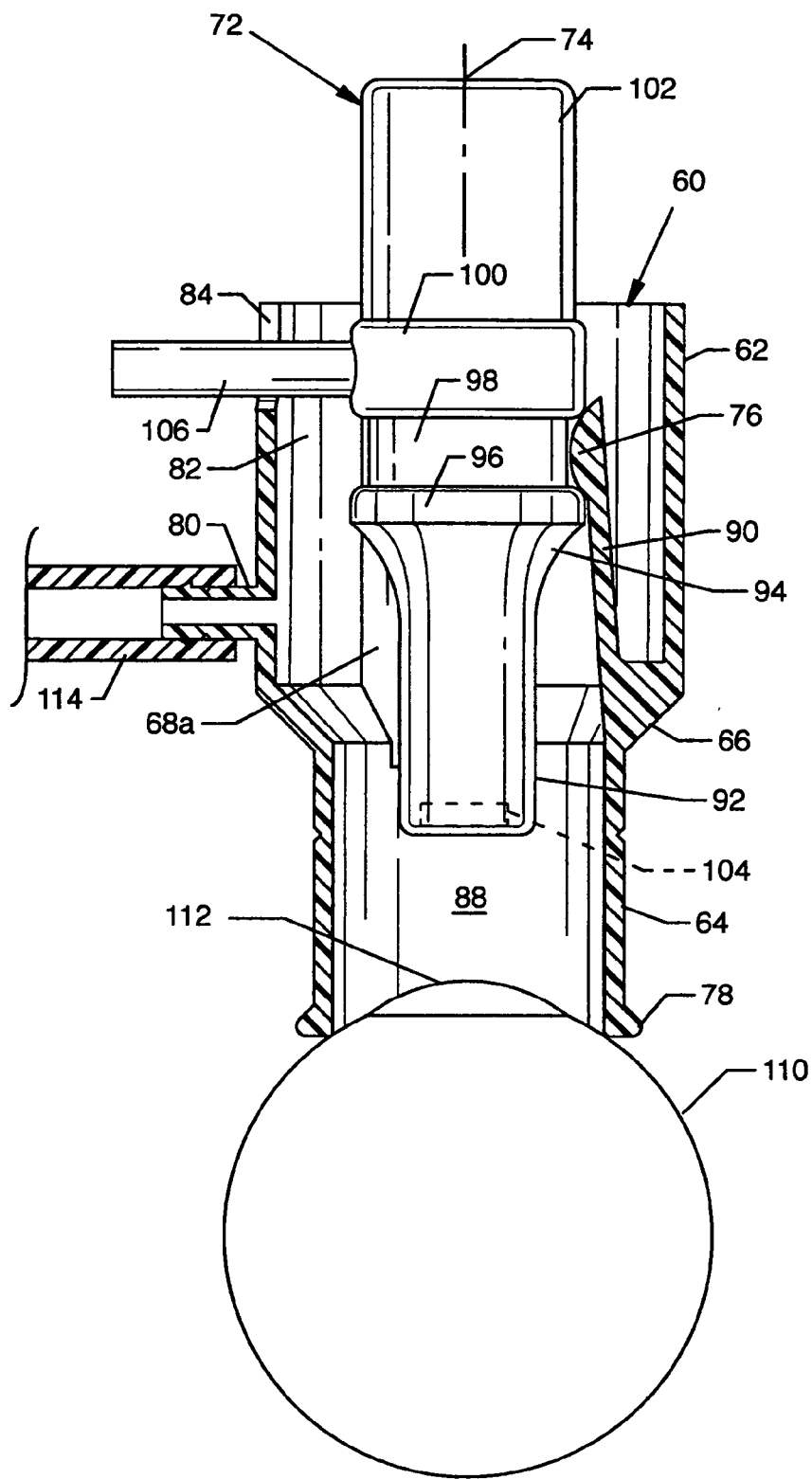
FIG. 15 illustrates the mode of operation where the ultrasound probe aligns within the alternative embodiment ultrasound probe positioning immersion shell incorporating the view of FIG. 11 for vertical alignment with and for ultrasound measurements of an eye (shown schematically); and, FIG. 16 illustrates the alignment and contact of the elements of the alternative embodiment ultrasound probe positioning immersion shell with the ultrasound probe.

FIG. 11 is a cross section view of the ultrasound probe positioning immersion shell 60 along line 11-11 of FIG. 10 showing the keeper tab 76 and the keeper arm 90 which supports the keeper tab 76. The keeper arm 90, which is flexible, is angled inwardly toward the central axis 74 in order to springingly and forcibly engage the ultrasound probe 72 by the interceding keeper tab 76, such as shown in FIG. 15. The keeper tab 76 includes an arcuate surface 76a which serves multiple uses, as shown in and as described in connection with FIG. 15.

Figure 12:
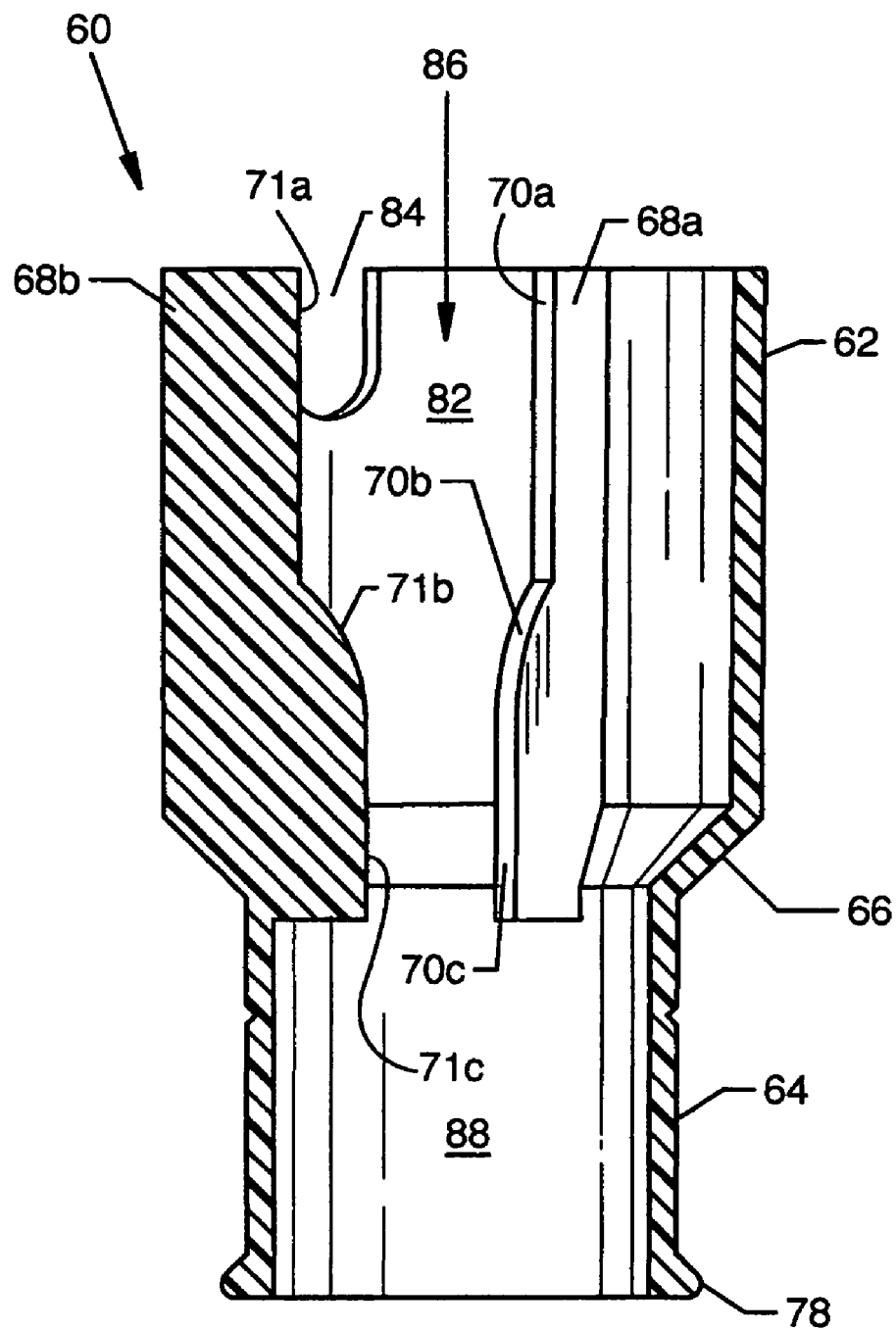
FIG. 12 is a cross section view of the alternative embodiment ultrasound probe positioning immersion shell along line 12-12 of FIG. 10.

FIG. 12 is a cross section view of the ultrasound probe positioning immersion shell 60 along line 12-12 of FIG. 10 showing the profile of the guide 68a including the upper guide edge 71a, the arcuate guide edge 71b and the lower guide edge 71c where the profile of the guide 68a and 68b are geometrically similar.

During insertion of a probe, such as ultrasound probe 72, the arcuate guide surface(s) 71b and 70b urge the lower region of the ultrasound probe 72 toward and into alignment along the central axis 74 of the ultrasound probe positioning immersion shell 60, as well as offer support to the ultrasound probe 72. Additional support of the ultrasound probe 72 is described later in detail.

Figure 13:
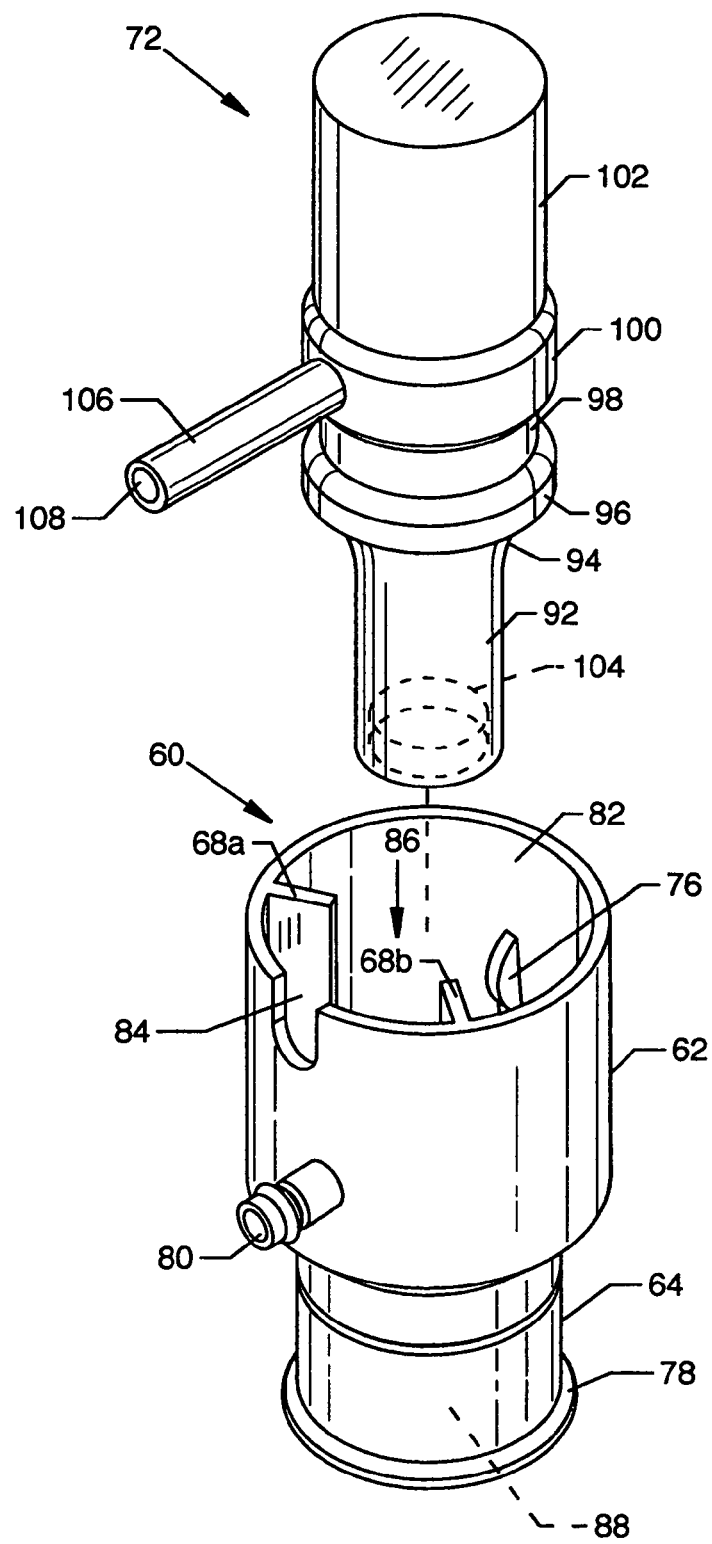
FIG. 13 illustrates an ultrasound probe in external alignment to the alternative embodiment ultrasound probe positioning immersion shell.

FIG. 13 illustrates an ultrasound probe 72 in external alignment to the ultrasound probe positioning immersion shell 60. Elements of the ultrasound probe positioning immersion shell 60 support the ultrasound probe 72 which is shown exterior to and which can be incorporated into use with the ultrasound probe positioning immersion shell 60. The ultrasound probe 72, as could other suitable probes, includes geometrically-shaped elements which are fittingly accommodated and positively engaged by the ultrasound probe positioning immersion shell 60, including elements of varying size and radii aligned along a central axis; however, other suitably-shaped elements incorporating other geometric configurations can be incorporated and shall not be deemed to be limiting as to the scope of ultrasound probes that can be incorporated into use with the present invention. One ultrasound probe that can be incorporated into use with the ultrasound probe positioning immersion shell 60, such as the ultrasound probe 72, is shown for purposes of demonstration and example, and includes an arrangement of geometrically configured elements including a lower constant radius body region 92 being generally cylindrical in shape, an arcuate annular region 94 extending from the lower constant radius body region 92, an annulus 96 having a smooth radiused edge extending from the arcuate annular region 94, an annular groove 98 extending from the annulus 96, an annulus 100 having smooth radiused edges extending from the annular groove 98, an upper constant radius body region 102 being generally cylindrical in shape extending from the annulus 100, and a transducer 104 at one end of the lower constant radius body region 92. Also included is a cable housing 106 and a passageway 108 for the conveyance of connection wire from the transducer 104 to external monitoring equipment.

MODE OF OPERATION

Figure 14:
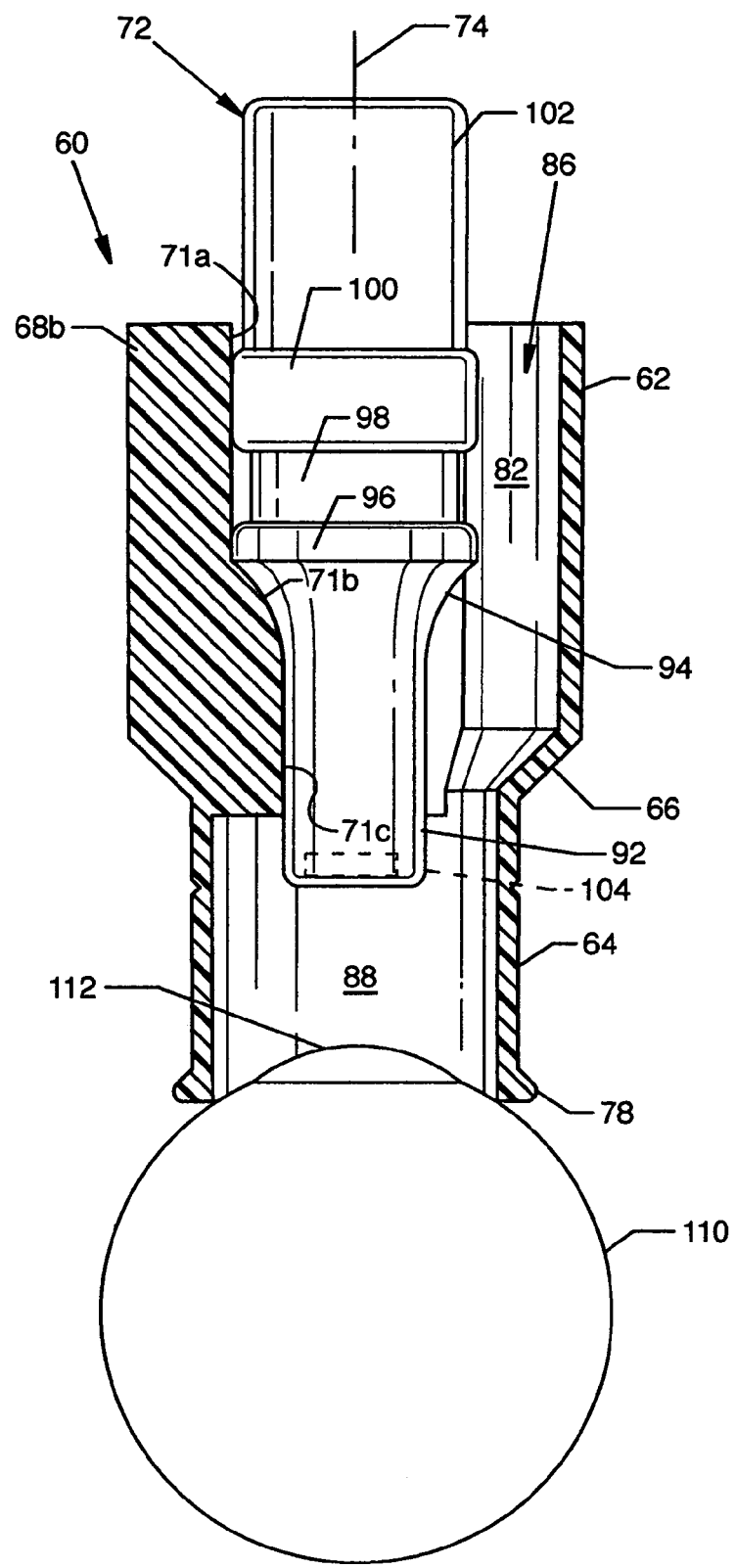
FIG. 14 illustrates the mode of operation where the ultrasound probe aligns within the alternative embodiment ultrasound probe positioning immersion shell incorporating the view of FIG. 12 for vertical alignment with and for ultrasound measurements of an eye (shown schematically)
Figure 16:
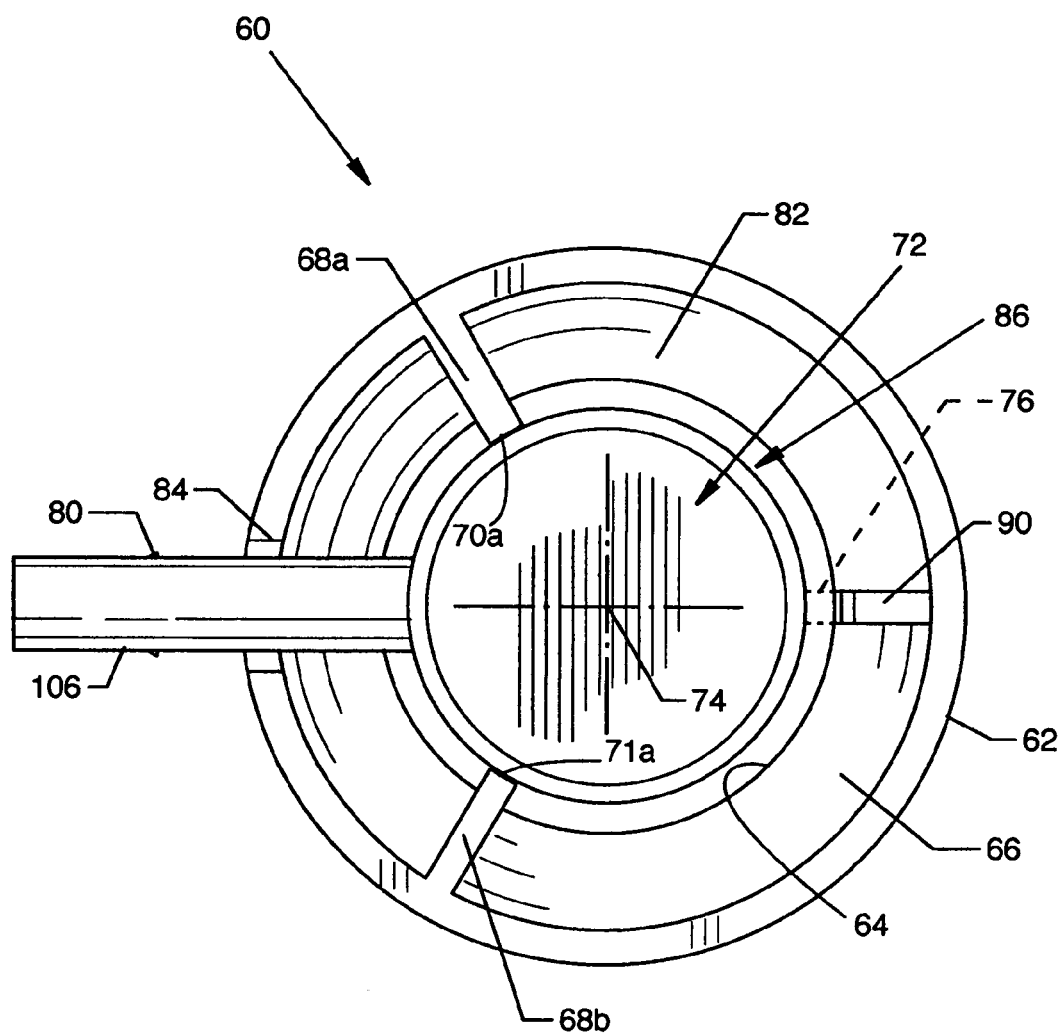

FIGS. 14, 15 and 16 best illustrate the mode of operation of the alternative embodiment where an ultrasound probe 72 aligns within the ultrasound probe positioning immersion shell 60 for vertical alignment with and for ultrasound measurements of an eye 110, including a cornea 112 where the limbus or area adjacent to the cornea 112 is in contact with the lip 78 of the ultrasound probe positioning immersion shell 60.

Insertion and guidance of the ultrasound probe 72 is initiated by alignment of the lower constant radius body region 92 with the ultrasound probe positioning immersion shell 60, such as indicated in FIG. 13.

FIG. 14 is the same view of the invention shown in FIG. 12 showing the accommodation of an ultrasonic probe, such as ultrasound probe 72. During insertion of the ultrasound probe 72, the lower constant radius body region 92 is initially guided and urged in one or more of several contactual situations. One such situation is where the lower constant radius body region 92 and/or the arcuate annular region 94 slidingly and guidingly can contact the keeper tab 76 (FIG. 15) and be urged toward and in a direction along the central axis 74. Such previous contact situation, which does not always occur but which can occur, is generally followed by the following contactual situation which can occur by itself or in following of the first contactual situation. Such a contactual situation is where the lower constant radius body region 92 and/or the arcuate circular region 94 can slidingly and guidingly contact the upper guide edge 70a and/or the upper guide edge 71a, where the lower constant radius body region 92 and/or the arcuate circular region 94 can slidingly and guidingly contact either or both of the arcuate guide edges 70b and/or 71b (arcuate guide edge 70b not shown), where the lower constant radius body region 92 slidingly and guidingly contacts the lower guide edge 71c and the lower guide edge 70c (lower guide edge 70c not shown) for guided and urged positioning toward and in a direction along the central axis 74. Any of the above situations separately, together, or in concert, guide, align and or support the ultrasound probe 72 in a position along and about the central axis 74, such as shown in FIG. 14, where the guides 68a and 68b provide support for an ultrasound probe, such as ultrasound probe 72. More specifically, the ultrasound probe 72 is supported at two or more elongated sites where the lower guide edges 70c and 71c provide for support of the lower constant radius body region 92, where the arcuate guide edges 70b and 71b provide for support of the arcuate annular region 94, and where the upper guide edges 70a and 71a provide for support of the annulus 96 and the annulus 100. FIG. 16 illustrates the alignment and contact of the elements of the ultrasound probe positioning immersion shell 60 with the ultrasound probe 72. Additional support and a securing means is also utilized with respect to FIG. 15.

FIG. 15 is the same view of the invention shown in FIG. 11 showing the securing of an ultrasonic probe, such as ultrasound probe 72, within the ultrasound probe positioning immersion shell 60. The keeper tab 76, including arcuate surface 76a, performs several uses and functions. One such use and function is for possible insertion and placement assistance of the lower region of ultrasound probe 72 by the keeper tab 76 during probe insertion into the ultrasound probe positioning immersion shell 60, as previously described. Another use and function is to forcibly secure the ultrasound probe 72 within the ultrasound probe positioning immersion shell 60; and another use and function is to force the ultrasound probe 72 against the guides 68a and 68b of the ultrasound probe positioning immersion shell 60 for alignment.

The ultrasound probe 72 is inserted into the ultrasound probe positioning immersion shell 60, as previously described, where during such insertion and alignment the keeper tab 76 is held toward the central axis 74 by the keeper arm 90. When the keeper tab 76 is in sliding contact with the transiting ultrasound probe 72, the keeper arm 90, which is oriented inwardly, maintains a position and orientation toward the central axis 74, so that the keeper tab 76 contacts the lower constant radius body region 92. Then, the keeper tab 76 subsequently and slidingly contacts the arcuate annular region 94, and finally intimately comes into forced tangential contact with the annulus 96 and the annulus 100 to reside generally in the annular groove 98 therebetween to force the probe 72 toward firm accommodated engagement with the guides 68a and 68b and appropriate elements thereof.

As previously described, the lower constant radius body region 92 of the ultrasound probe 72 aligns to the guide edges of the guides 68a-68b and along the central axis 74 of the ultrasound probe positioning immersion shell 60 a distance along the central axis 74 which is predetermined by the relationship of the arcuate guide edges 70b and 71b to the arcuate annular region 94 and the length of the lower constant radius body region 92 of the ultrasound probe 72 to position the transducer 104 of the ultrasound probe 72 the correct and suitable distance from the cornea 112 of the eye 110. Correspondingly, the arcuate edge guides 70b and 71b act as stops which stoppingly engage the arcuate annular region 94 of the ultrasound probe 72. Full support of the ultrasound probe 72 is provided at several areas, promoting stability of the ultrasound probe 72 with respect to the ultrasound probe positioning immersion shell 60, as described.

A filler tube 114, such as shown in FIG. 15, can frictionally engage the fluid transfer port 80, or can frictionally engage and incorporate adhesive to permanently secure to the fluid transfer port 80 for introduction of saline solution or other suitable solution, such as, but not limited to, such method previously described. The invention user can directly observe correct placement of the ultrasound probe positioning immersion shell 60 on the eye 110 since the liquid filling apparatus and the fluid transfer port 80 of the ultrasound probe positioning immersion shell 60 are located on the upper cylindrical body 62 away from the lower cylindrical body 64 and away from the surface of the eye 110. Correct placement of the ultrasound probe positioning immersion shell 10 can be further enhanced by the use of a clear plastic to form the structure of the invention. The use of clear plastic also enhances level monitoring of the liquid medium. The fluid transfer port 80 of the ultrasound probe positioning immersion shell 60 allows for the operator to use different means of supplying the liquid medium. Liquid medium, such as a saline solution, can be filled through the fluid transfer port 80 by a syringe through the fluid transfer port 80 or by a syringe through the filler tube 114. Alternatively, the fluid transfer port 80 could be simply a hole, such as the fluid transfer port 26 shown in FIGS. 1 and 2, and utilized in the same fashion incorporating the use of the hole itself as an injection port, or by the use of other devices connected thereto, thereby incorporating the use of a Luer fitting, a fitted filler tube, a vial directly attached to the fluid transfer port 80, a Luer adapter and tubing attached to the fluid transfer port 80 which is connected to a container of liquid medium, or by other suitable delivery methods known in the art.

Introduction and flow of saline solution (liquid medium) into and within the ultrasound probe positioning immersion shell 60 is unrestricted, first into the upper chamber 82, followed by passage or draining of saline solution through and along the vent 86 into the lower chamber 88 for suitable immersion of the lower portions of the ultrasound probe 72, including at least the transducer 104 and preferably other portions of the ultrasound probe 72. As saline solution enters the upper chamber 82 and subsequently the lower chamber 88, air residing in the upper chamber 82 and the lower chamber 88 is displaced by the incoming saline solution and vented and expelled without restriction from the lower chamber 88, and through the upper chamber 82, and through the top of the upper chamber 82 (i.e., through the vent 86). Fully vented upper and lower chambers 82 and 88 prevent back pressure buildup so that outflow of displaced air and exclusion of bubbles is not impeded.

The large volumetric capacity of the internal vent 86 disperses the liquid flow pattern and creates a sufficiently large path for the saline solution to drain in one direction and for air to escape in another direction to and from the lower chamber 88 simultaneously, thereby minimizing air bubble formation in the lower chamber 88 to provide bubble-free saline solution between the transducer 104 of the ultrasound probe 72 and the cornea 112 and surrounding surface of the eye 110.

Various modifications can be made to the present invention without departing from the apparent scope thereof.

The invention claimed is:

1. An ultrasound probe positioning immersion shell for use between an ultrasound probe having a transducer with a body region adjacent the transducer and a human eye with a cornea, the shell comprising:
   a. an upper cylindrical body tapering, at a tapered region, to a lower cylindrical body, the upper and lower cylindrical bodies defining a central axis, an upper chamber and a lower chamber;
   b. an external guide ring extending across an upper region of the upper cylindrical body, the external guide ring including:
      (1) a plurality of external guide surfaces extending through the external guide ring, each of the external guide surfaces spaced a like radius from and centered along the central axis; and,
      (2) a plurality of external vents extending through the external guide ring;
   c. a fluid transfer port extending through the upper cylindrical body to communicate with an upper chamber;
   d. an internal guide ring, interior to the tapered region and between the upper and lower chambers, the internal guide ring including:
      (1) a plurality of internal guide surfaces extending through the internal guide ring, each of the internal guide surfaces spaced a like radius, less than the like radius of the external guide surfaces, from and centered along the central axis; and,
      (2) a plurality of internal vents extending through the internal guide; and,
   e. a lip, for contacting the human eye about the cornea of the eye, the lip situated at a lower extreme of the lower cylindrical body.

2. The shell of claim 1, further comprising a threaded hole in the upper cylindrical body.

3. The shell of claim 1, wherein each of the external guide surfaces of the plurality of external guide surfaces are arcuate.

4. The shell of claim 3, wherein each of the external vents of the plurality of external vents are arcuate and intersect at least two external guide surfaces of the plurality of external guide surfaces.

5. The shell of claim 4, wherein each of the arcuate external vents of the plurality of arcuate external vents has a common offset from the central axis.

6. The shell of claim 1, wherein each of the internal guide surfaces of the plurality of internal guide surfaces are arcuate.

7. The shell of claim 6, wherein each of the internal vents of the plurality of internal vents are arcuate and intersect at least two internal guide surfaces of the plurality of internal guide surfaces.

8. The shell of claim 7, wherein each of the arcuate internal vents of the plurality of arcuate internal vents has a common offset from the central axis.

9. The shell of claim 1, wherein the external guide ring is radially symmetrical about the central axis.

10. The shell of claim 1, wherein the internal guide ring is radially symmetrical about the central axis.

11. The shell of claim 1, wherein the plurality of external guide surfaces and the plurality of internal guide surfaces are radially symmetrical about the central axis.

12. The shell of claim 1, wherein the lip is radially symmetrical about the central axis.

13. The shell of claim 1, wherein the plurality of external guide surfaces and the plurality of internal guide surfaces interact with the tapered body so as to firstly, guidingly and slidingly vertically align, during insertion, and then secondly, stoppingly position the ultrasound probe, once appropriately inserted, at a predetermined aligned and spaced distance relationship relative to the lip.

14. The shell of claim 1, wherein the fluid transfer port includes a Luer lock fitting.

15. The shell of claim 14, wherein the Luer lock is a male fitting.

16. The shell of claim 14, wherein the Luer lock is a female fitting.

17. The shell of claim 1, wherein the shell is a one-piece shell.

18. The shell of claim 1, wherein the shell is formed of metal.

19. The shell of claim 18, wherein the shell is formed by machining.

20. The shell of claim 18, wherein the metal is selected from the group consisting of stainless steal and aluminum.

21. The shell of claim 1, wherein the shell is formed of polymer.

22. The shell of claim 21, wherein the shell is formed by injection molding.

23. The shell of claim 21, wherein the polymer is selected from the group consisting of acrylic and polycarbonate.

24. The shell of claim 23, wherein the shell is formed of polycarbonate ULTEM.

25. The shell of claim 21, wherein the polymer is a transparent or opaque polymer.

26. The shell of claim 1, wherein the shell is transparent or opaque.

27. An ultrasound probe positioning immersion shell for use between an ultrasound probe having a transducer with elements of varying size and radii aligned along body with a central axis adjacent to the transducer and a human eye with a cornea, the shell comprising:
   a. an upper cylindrical body tapering, at a tapered intermediate body, to a lower cylindrical body, the upper and lower cylindrical bodies defining a central axis, an upper chamber and a lower chamber;
   b. a plurality of guides extending inwardly from the upper cylindrical body and tapered intermediate body and lower cylindrical body, each guide of the plurality of guides having an inwardly facing upper guide edge and an inwardly facing lower guide edge, the inwardly facing lower guide edge offset from the central axis less than the inwardly facing upper guide edge, the upper and lower guide edges defining a predefined inserted and aligned position for the ultrasound probe;

c. a plurality of vents, at least one vent of the plurality situated between guides of the plurality of guides, the vents of the plurality of vents communicating between the lower chamber and the upper chamber;

d. a fluid transfer port extending through the upper or lower cylindrical body to communicate with an upper chamber; and, e. a lip, for contacting the human eye, the lip situated at a lower extreme of the lower cylindrical body.

28. The shell of claim 27, further comprising a continuous sliding surface extending along at least one of the guides of the plurality of guides, the continuous sliding surface further defining the predefined inserted and aligned position for the ultrasound probe.

29. The shell of claim 28, wherein the continuous sliding surface is arcuate.

30. The shell of claim 27, wherein the ultrasound body has an arcuate annulus and further comprising a keeper tab, the keeper tab springingly, resiliently, biased inwardly from the upper cylindrical body, so as to engage the arcuate annulus when the ultrasound probe occupies the predefined inserted and aligned position.

31. The shell of claim 30, wherein the keeper tab springingly, resiliently, biases a probe toward and against the guide surfaces.

32. The shell of claim 30, wherein the keeper tab stoppingly engages the arcuate annulus.

33. The shell of claim 27, wherein the inwardly directed guide edges mate with and stoppingly accommodate the ultrasound probe.

34. The shell of claim 27, further comprising a threaded hole in the upper cylindrical body.

35. The shell of claim 27, wherein each of the external guide surfaces of the plurality of external guide surfaces are arcuate.

36. The shell of claim 27, wherein the fluid transfer port includes a Luer lock fitting.

37. The shell of claim 36, wherein the Luer lock is a male fitting.

38. The shell of claim 36, wherein the Luer lock is a female fitting.

39. The shell of claim 27, wherein the shell is a one-piece shell.

40. The shell of claim 27, wherein the shell is formed of metal.

41. The shell of claim 40, wherein the shell is toned by machining.

42. The shell of claim 40, wherein the metal is selected from the group consisting of stainless steel and aluminum.

43. The shell of claim 27, wherein the shell is toned of polymer.

44. The shell of claim 43, wherein the shell is formed by injection molding.

45. The shell of claim 43, wherein the polymer is selected from the group consisting of acrylic and polycarbonate.

46. The shell of claim 45, wherein the shell is formed of polycarbonate ULTEM.

47. The shell of claim 43, wherein the polymer is a transparent or opaque polymer.

48. The shell of claim 27, wherein the shell is transparent or opaque.

49. A method of positioning an ultrasound probe, the ultrasound probe including a transducer and a body adjacent the transducer, relative to a human eye with a cornea, the method comprising the steps of:

a. providing a shell, the shell including:

(1) a body with an upper chamber and a lower chamber;

(2) guide means defining a predetermined inserted position for the transducer and the body region adjacent the transducer, such that, in the predetermined inserted position, the transducer is located in the lower chamber and oriented for distance measurement;

(3) vent means communicating between the upper chamber and the lower chamber;

(4) a fluid transfer port extending through the body to communicate with the upper chamber; and, (5) a lip, for contacting the human eye, the lip situated at a lower extreme of the lower chamber defined by the body;

b. inserting the ultrasound probe into the shell until the predetermined inserted position is achieved; and, c. placing the shell on the human eye, with the lip about the cornea.

50. The method of claim 49, wherein the step of inserting precedes the step of placing.

51. The method of claim 49, wherein the step of placing precedes the step of inserting.

52. The method of claim 49, wherein the shell is transparent and the method further includes the step of visually verifying the placing step by observing the cornea within the lip.

53. The method of claim 49, further comprising the step of filling the lower chamber with media by injecting media through the fluid transfer port.

54. The method of claim 53, further including the step of measuring a distance of the eye through the cornea with the transducer of ultrasound probe subsequent to the filling step.

55. The method of claim 53, wherein the media fills between the cornea and the transducer of the ultrasound probe as a result of the filling step.

56. The method of claim 53, wherein air is displaced through the venting means during the filling step.

57. The method of claim 49, wherein the shell further includes sliding means to direct the ultrasound probe to the predetermined inserted position.

58. The method of claim 49, wherein the shell further includes keeper means to retain the ultrasound probe in the predetermined insertion position.

* * * * *